United States Patent
Gong

(10) Patent No.: US 10,781,234 B2
(45) Date of Patent: Sep. 22, 2020

(54) MACROCYCLIC COMPOUNDS AND METHODS OF MAKING AND USING SAME

(71) Applicant: THE RESEARCH FOUNDATION FOR THE STATE UNIVERSITY OF NEW YORK, Buffalo, NY (US)

(72) Inventor: Bing Gong, Amherst, NY (US)

(73) Assignee: The Research Foundation for The State University of New York, Buffalo, NY (US)

( * ) Notice: Subject to any disclaimer, the term of this patent is extended or adjusted under 35 U.S.C. 154(b) by 0 days.

(21) Appl. No.: 15/763,259

(22) PCT Filed: Aug. 18, 2017

(86) PCT No.: PCT/US2017/047675
§ 371 (c)(1),
(2) Date: Mar. 26, 2018

(87) PCT Pub. No.: WO2018/035496
PCT Pub. Date: Feb. 22, 2018

(65) Prior Publication Data
US 2019/0135866 A1 May 9, 2019

Related U.S. Application Data

(60) Provisional application No. 62/376,750, filed on Aug. 18, 2016.

(51) Int. Cl.
| | | |
|---|---|---|
| C07K 7/64 | (2006.01) |
| C07K 14/60 | (2006.01) |
| C07D 259/00 | (2006.01) |
| C08L 77/02 | (2006.01) |
| A61K 38/00 | (2006.01) |
| C08L 77/04 | (2006.01) |

(52) U.S. Cl.
CPC .............. *C07K 7/64* (2013.01); *C07D 259/00* (2013.01); *C07K 14/60* (2013.01); *C08L 77/02* (2013.01); *A61K 38/00* (2013.01); *C08L 77/04* (2013.01); *C08L 2203/02* (2013.01)

(58) Field of Classification Search
None
See application file for complete search history.

(56) References Cited

U.S. PATENT DOCUMENTS

2009/0264345 A1  10/2009  McAlpine et al.
2016/0137710 A1   5/2016  Kawahata et al.

OTHER PUBLICATIONS

Zeng, Jisen et al, "Interplay of olefin metathesis and multiple hydrogen bonding interactions: covalently cross-linked zippers." Org. Lett. (2011) 13(15) p. 3798-3801.*
Sengupta, Durba et al, "Toroidal pores formed by antimicrobial peptides show significant disorder." Biochem. Biophys. Acta (2008) 1778 p. 2308-2317.*
Jean-François, Frantz et al, "Pore formation induced by an antimicrobial peptide: electrostatic effects." Biophysical J. (2008) 95 p. 5748-5756.*
Zhu, Y-Y., et al., Hydrogen-Bonded Aryl Amide Macrocycles: Synthesis, Single-Crystal Structures, and Stacking Interactions with Fullerenes and Coronene, Journal of Organic Chemistry, 2008, vol. 73, No. 5, pp. 1745-1451, abstract only.
Bagnacani, V., et al., Arginine clustering on calix[4]arene macrocycles for improved cell penetration and DNA delivery, nature Communications, 2013, vol. 4, No. 1721, pp. 1-7.
Pubchem CID 10819332, Oct. 26, 2006, pp. 1-10.

* cited by examiner

*Primary Examiner* — Fred H Reynolds
(74) *Attorney, Agent, or Firm* — Hodgson Russ LLP

(57) ABSTRACT

Provided are macrocyclic compounds having one or more transmembrane segment-thermoresponsive segment moiety. Also provided are dimers comprising two macrocyclic units, which have one or more transmembrane segment-thermoresponsive segment moiety, joined by one or more cross-linking moieties. The macrocyclic compounds and macrocyclic units have a macrocyclic backbone comprise alternating alpha amino acid and meta-aminobenzoic acid moieties. The macrocyclic compounds and dimers can be used to deliver a cargo (e.g., cell-interacting agents such as, for example, drugs and cryoprotectants) to, for example, an organ, tissue, or an individual, A cargo may be encapsulated in lipid vesicles.

15 Claims, 17 Drawing Sheets
Specification includes a Sequence Listing.

(a) *Oligoether [oligo(butylene glycol)] chains*

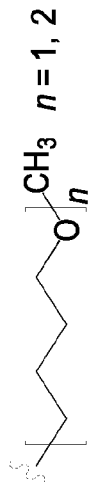

(b) *Amphiphilic peptide strands*

Extended beta-strands with 10 to 12 amino acid residues:

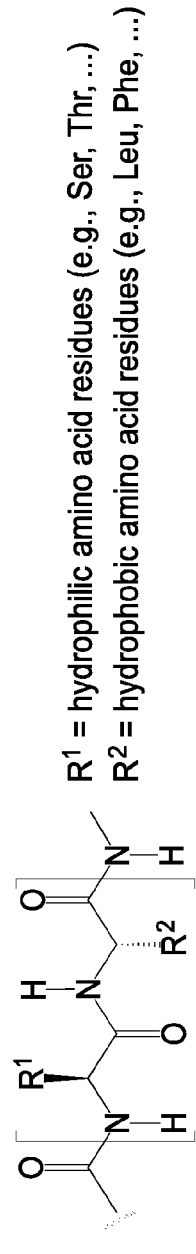

$R^1$ = hydrophilic amino acid residues (e.g., Ser, Thr, ....)
$R^2$ = hydrophobic amino acid residues (e.g., Leu, Phe, ....)

Oligopeptides with 24-27 amino acid residues that fold into amphiphilic alpha-helices (i.e., helices with one hydrophilic and one hydrophobic face)

(c) *Other amphiphilic structures*

Examples: Derivatives of chloic acid;
synthetic chain-, rod-, or tape-like molecules with one hydrophilic and one hydrophobic edge

Figure 5

(a) Thermoresponsive linker based on elastin-like pepetides (ELP)

For example:

HSCH$_2$CO-NH((VPGVG)$n$CONH-CH$_2$CH$_2$-NHCO(GVGOV)$n$NHCO-CH$_2$SH, $n$ = 2-5

HS-ELP-SH

ELP chains with other amino acid sequences can be similarly adopted.

(b) Thermoresponsive linker based on thermoresponsive polymers

For example, linker based on poly(*N*-isopropylacrylamide):

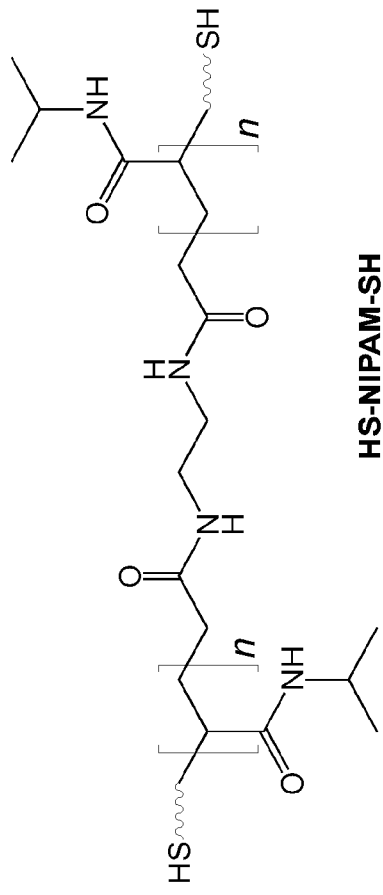

HS-NIPAM-SH

Other thermoresponsive ploymer chains can be similarly adopted.

Figure 6

1. Macrocyclic portal:
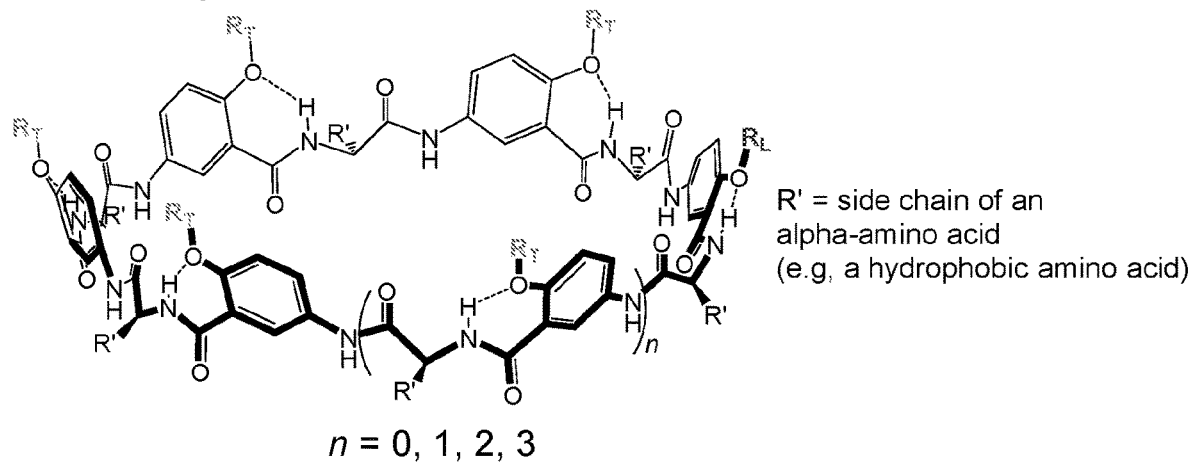
R' = side chain of an alpha-amino acid
(e.g., a hydrophobic amino acid)
$n = 0, 1, 2, 3$
2. Membrane-compatible "tentacles":
or other structures suitable as transmembrane segments
Figure 15

3. Covalent linker (tether) connecting two macrocyclc portas:

$R_L$ =  (containing a photo-responsive or thermo-responsive moiety)

(a) Termo-responsive linker (with lengths responsive to tempaterature)

        e.g., linker based on ELPs:

(extended at low temp)    (shrinked at high temp)    $(VPGVG)_{3-5}$
or other thermo-responsive oligomers or polymers

(b) Photo-responsive moiety (with conformations responsive to light)

e.g., photo-responsive moeties:

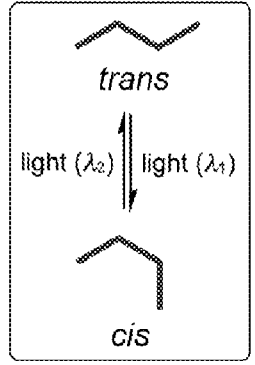

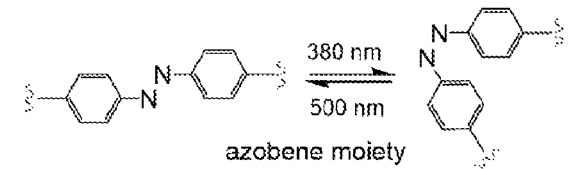

azobene moiety

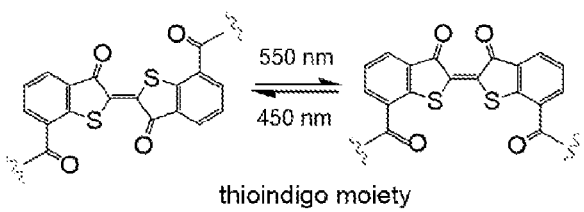

thioindigo moiety

Figure 15 (cont.)

MACROCYCLIC COMPOUNDS AND METHODS OF MAKING AND USING SAME

CROSS REFERENCE TO RELATED APPLICATIONS

This application claims priority to U.S. Provisional Application No. 62/376,750, filed on Aug. 18, 2016, the disclosure of which is hereby incorporated by reference.

FIELD OF THE DISCLOSURE

The disclosure generally relates to macrocyclic compounds with pendant groups that can interact with cell membranes. More particularly the disclosure generally relates to macrocyclic compounds comprising one or more transmembrane segment-thermoresponsive segment groups.

BACKGROUND OF THE DISCLOSURE

The plasma membrane plays vital biological roles by serving as a permeability barrier that prevents unassisted movement of most water-soluble substances and thus maintains the characteristic differences between the inside and outside of the cell. In biological systems, the permeability of cell membrane is regulated by passive pores driven along, and by active transporters against, the concentration gradient.

Efforts to create synthetic channels started three decades ago and are still ongoing, with the majority of systems being on ion transport and few on molecular transport. Compared to protein pores, synthetic organic pores offer unique advantages including substantially smaller molecular masses, synthetic tunability allowing the incorporation of structural units that otherwise are incompatible with or cannot be incorporated into protein-based pores, high stability, and non-immunogenicity. However, due to the limitations of current synthetic methods, the architectural variability of membrane proteins remains widely unexplored and inaccessible to synthetic constructs. In fact, designs of large functional pores that can be readily synthesized with minimal help from biological approaches are remarkably rare.

The controlled poration of plasma membranes can revolutionize many important applications related to the transport of impermeable hydrophilic substances across cell membranes. Applications that will benefit include drug delivery by releasing the contents of capsules like liposomes, biotherapeutics by permeabilizing cells to cytotoxic drugs, or biopreservation by loading cells with bioprotective agents.

For example, cryopreservation, which offers a revolutionizing opportunity to achieve long-term biobanking, is one such application that requires the controlled transport of hydrophilic substances called cryoprotective agents (CPAs). In nature, species including microorganisms, plants, insects, fish, and amphibians can survive at ultralow temperature with controlled ice growth to form stable glasses in which the intracellular medium contains high concentrations of saccharides (particularly glucose, trehalose and sucrose) and glycols to protect from chilling injury. Inspired by nature, small molecule CPAs have been widely applied in cryopreservation by biologists. However, a successful preservation and restoration of a medically relevant organ has not occurred. In mammalian cells, intracellular CPA concentration is limited due to cellular regulation, thus outsourcing is required to transport 1.0-2.0M CPAs across cell membrane during cryopreservation. This remains a significant challenge.

Biological ion and molecular channels play many functions that are vital to the survival of cells and organisms. At low (sub-zero) temperatures, the effectiveness of most biologically and medically important hydrophilic substances (such as CPAs or other therapeutics) is impeded due to the fact that biological channels, e.g. glucose transporters (GLUTs) and aquaporins typically become dysfunctional and can no longer serve as gates for transporting these substances. Long loading time and disruptive localized pressure is often required to reach effective intracellular concentration. As a circumstance, either the needed concentration of the therapeutic agent cannot be reached or the cell can experience detrimental shrinkage caused by dehydration and undergoapoptosis after thawing. This is more lethal for large complex solid organs/tissues compared to single cells as the functional junctions between cells are permanently damaged. For instance, the upload of CPAs to rabbit kidney during vitrification process can take up to 3 hours as the loading rate significantly decreases while temperature drops, which surges toxicity level and post-thaw death rate.

The use of natural pore-forming proteins for intracellular delivery of hydrophilicmolecules such as sugars has shown promise. It was previously demonstrated that intracellular delivery of 0.2M trehalose significantly improved post-thaw cell viability when transported through a genetically engineered variant of the pore forming toxin, α-hemolysin. The large lumen of α-hemolysin (14 Å) can allow sufficient transport of large molecules like trehalose, but replaces adverse CPA cytotoxicity with cytotoxicity based-upon a lack of selective transport and large pore size, especially at physiological temperature. A rational blockage strategy was critical to reduce toxicity and the genetically engineered pore forming protein based on α-hemolysin was blocked with addition of $Zn^{2+}$ ion for 18 hours. Overcoming the deficiencies of natural protein pores by developing synthetic pores capable of mimicking natural systems has attracted the interest of many chemists over the last several decades. These channels and pores provide significant advantages such as synthetic efficiency and structure diversity to engineer various functions such as responsiveness and selective transport. Most known systems are focused on selective ion transport with few capable of transporting molecules.

SUMMARY OF THE DISCLOSURE

In an aspect, the macrocyclic compounds and comprise a macrocyclic backbone and one or more transmembrane segment-thermoresponsive segment groups. A transmembrane segment-thermoresponsive segment group comprises a transmembrane segment covalently bound to a thermoresponsive segment. The transmembrane segment-thermoresponsive segment groups can be referred to as "tentacles" (e.g., R groups in the example macrocycle structure below). The macrocyclic compounds have pendant groups (transmembrane segment-thermoresponsive segment groups) that can interact with cell membranes and form membrane-spanning unimolecular pores. The macrocyclic backbone comprises a plurality of moieties comprising an alpha-amino acid moiety (residu/moiety) and a meta-aminobenzoic acid moiety that form a macrocyclic structure.

The transmembrane segment of the transmembrane segment-thermoresponsive segment group is a moiety covalently bound to the macrocyclic backbone. A transmembrane segment can comprise a transmembrane moiety. The transmembrane segment/moiety can interact with a cell (plasma) membrane.

A thermoresponsive segment is a moiety/group covalently bound to an end of the transmembrane segment that not covalently bound to the macrocyclic backbone (e.g., opposite or remote to a terminus of the transmembrane segment bound to the macrocyclic backbone). A thermoresponsive segment can have a thermoresponsive moiety. A thermoresponsive segment (e.g., thermoresponsive moiety) has features (e.g., structural features) or properties that are altered in different thermal environments.

Macrocyclic compounds can comprise additional compounds (cargo) in the interior space defined by the tentacles in the closed configuration. For example, a macrocycle comprises one or more additional compound Examples of additional compounds include drugs, imaging agents, and the like. The additional compounds can be hydrophilic.

In various examples, a dimer, which can be referred to as a pore-forming compound, comprising two macrocyclic moieties/groups derived from macrocyclic compounds of the present disclosure covalently bound to each other through one or more covalent bonds that connect the bottoms of the two macrocyclic units (e.g., two crosslinked macrocyclic compounds of the present disclosure). The covalent bond(s) can be referred to as crosslinking bonds.

The macrocyclic compounds and dimers of the present disclosure can be referred to as pore-forming compounds. When contacted with a cell (plasma) membrane the macrocyclic compounds or dimers can form a pore (e.g., pore structure) in the cell membrane that provides fluid contact between the extracelluar space and intracellular space. Pores formed by the pore-forming compounds on, partially within, or within the plasma membrane serve as "doors" that allow the controllable release of a cargo (e.g., hydrophilic therapeutic agents (e.g., drugs) and cell-protective agents (e.g., cryoprotectants) that may be encapsulated inside vesicles (liposomes). In various examples, the drugs and cell-protective reagents are hydrophilic drugs that cannot penetrate the cell membranes.

In an aspect, the present disclosure provides compositions comprising one or more macrocyclic compound and/or one or more dimer (e.g., pore-forming compound) of the present disclosure. For example, a composition comprising one or more macrocyclic compound more macrocyclic compound and/or one or more dimer (e.g., pore-forming compound) of the present disclosure can be used in a method of cryopreservation.

In an aspect, the present disclosure provides methods of making macrocyclic compounds and dimers of the present disclosure. Methods of making macrocyclic compounds and dimers of the present disclosure are provided herein.

In an aspect, the present disclosure provides uses of macrocyclic compounds, dimers, and compositions of the present disclosure. For example, macrocyclic compounds can be used in cryopreservation methods, methods of delivering (e.g., controlled/selective delivery) or release of drugs, nutrients, imaging agents, radioactive or fluorescent tracers, or a combination thereof, as membrane-bond sensor molecules and ions (e.g., in methods for detecting chemical or biological warfare-like toxic proteins and bacteria such as, for example, anthrax), as nano-containers for catalyzing chemical reactions, and as arrays (membranes) of nanopores (which can be used as, for example, materials for or in methods of separation and purification of, for example, molecules and ions).

BRIEF DESCRIPTION OF THE FIGURES

For a fuller understanding of the nature and objects of the disclosure, reference should be made to the following detailed description taken in conjunction with the accompanying figures.

FIG. 1 also shows the tentacles attached to the rigid macrocyclic template consist of a membrane-spanning (purple) and temperature responsive (blue) segment. FIG. 1 also shows the general structure of a channel-former. FIG. 1 also shows the specific design of the tentacle (R) and α-amino acid residues (R') to be adopted.

FIG. 5 shows structural designs of membrane-interacting tentacles.

FIG. 6 shows structures of thermo-responsive linkers.

FIG. 15 shows examples of dimers (e.g., photo- and thermoresponsive transmembrane pore-formers).

DETAILED DESCRIPTION OF THE DISCLOSURE

Figure 1:
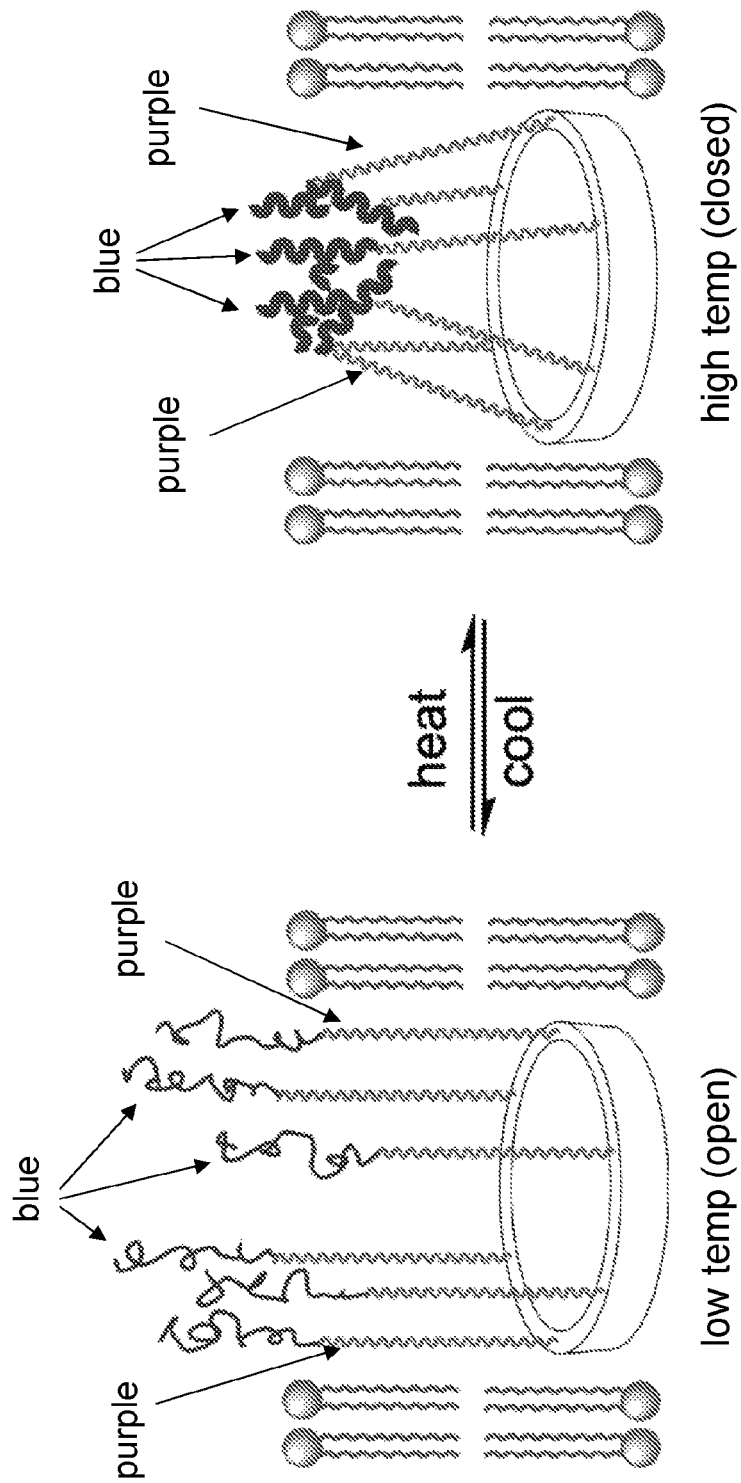
FIG. 1 shows a schematic illustration of a macrocyclic compound of the present disclosure, which is a molecular channel-former.

Although claimed subject matter will be described in terms of certain examples and embodiments, other examples and embodiments, including examples and embodiments that do not provide all of the benefits and features set forth herein, are also within the scope of this disclosure. Various structural, logical, process step, and electronic changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

As used herein, the term "moiety", unless otherwise stated, refers to a chemical entity that has two or more termini that can be covalently bonded to other chemical species. Examples of moieties include, but are not limited to:

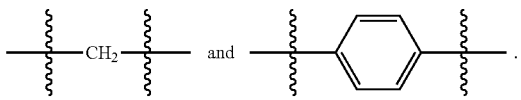

As used herein, the term "group", unless otherwise stated, refers to a chemical entity that has a terminus that is covalently bonded to other chemical species. Examples of groups are provided herein.

As used herein, the term "alkyl group", unless otherwise stated, refers to branched or unbranched hydrocarbons. An alkyl group can be saturated. Examples of such alkyl groups include methyl groups (—$CH_3$), ethyl groups, propyl groups, butyl groups, isopropyl groups, tert-butyl groups, and the like. For example, the alkyl group can be a $C_5$-$C_8$ alkyl group including all integer numbers of carbons and ranges of numbers of carbons there between. The alkyl group can be unsubstituted or substituted with one or more substituent. Examples of substituents include, but are not limited to, various substituents such as, for example, halogens (—F, —Cl, —Br, and —I), aliphatic groups (e.g. alkyl groups, alkenyl groups, and alkynyl groups), alkoxyl groups, carboxyl/carboxylate groups, ether groups, thiol groups, amine groups, amide groups, and the like, and combinations thereof.

The present disclosure provides macrocyclic compounds and dimers formed from the macrocyclic compounds and macrocyclic units derived from the macrocyclic compounds. The present disclosure also provides uses of the macrocyclic compounds and dimers.

In an aspect, the macrocyclic compounds comprise a macrocyclic backbone and one or more transmembrane segment-thermoresponsive segment groups. A transmembrane segment-thermoresponsive segment group comprises a transmembrane segment covalently bound to a thermoresponsive segment. The transmembrane segment-thermoresponsive segment groups can be referred to as "tentacles" (e.g., R groups in the example macrocycle structure below. The macrocyclic compounds have pendant groups (transmembrane segment-thermoresponsive segment groups) that can interact with cell membranes and form membrane-spanning unimolecular pores (which are also referred to as molecular pores and nanopores).

The macrocyclic backbone comprises a plurality of moieties comprising an alpha-amino acid moiety (residu/moiety) and a meta-aminobenzoic acid moiety that form a macrocyclic structure. For example, a moiety (e.g., repeat unit) comprising an alpha-amino acid moiety and a meta-aminobenzoic acid moiety has the following structure:

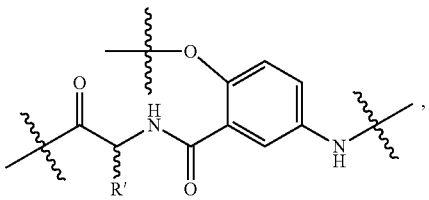

where R' is a side-chain of an alpha-amino acid and the phenyl moiety can be substituted as described herein. The alpha-amino acid moieties can be derived from naturally occurring amino acids (except D- or L-proline) and/or non-naturally occurring amino acids. The moieties comprising the alpha amino acid and meta-aminobenzoic acid moiety in the macrocyclic backbone can be the same moieties or any combination of moieties (i.e., a combination of alpha-amino acid side chains and/or substituted/unsubstituted meta-aminobenzoic acid moieties). For example, a macrocyclic backbone has 5 to 8 moieties comprising an alpha-amino acid moiety and a meta-aminobenzoic acid moiety. The relative amounts of naturally occurring amino acids and/or non-naturally occurring amino acids can be selected for a desired biodegradability of the macrocycle. In an example, the amino acids are not proline (e.g., D- or L-proline). In another example, the macrocyclic backbone does not comprise any moieties derived from proline (e.g., D- or L-proline).

The transmembrane segment of the transmembrane segment-thermoresponsive segment group is a moiety covalently bound to the macrocyclic backbone. A transmembrane segment can comprise a transmembrane moiety. The transmembrane segment/moiety can interact with a cell (plasma) membrane. It is desirable that the transmembrane segment (e.g., transmembrane moiety) have a hydrophobic character suitable for interaction with the interior of a mammalian cell membrane (e.g., are compatible with the hydrophobic interior of mammalian cell membranes (e.g., lipid bilayers)). Transmembrane segments can be covalently bound to the macrocyclic backbone through various functional moieties. A transmembrane segment can be covalently bound to the macrocyclic backbone through, for example, an ether moiety (—O—). The transmembrane segment can include a linking moiety that connects a transmembrane moiety to the macrocyclic backbone and/or thermoresponsive segment (e.g., via a functional moiety) or the functional moiety that covalently connects the macrocyclic backbone to the transmembrane segment. It is desirable that the transmembrane segment has a length that spans typical cell membranes. For example, a transmembrane segment has a length of 3 to 5 nm. In the case of a dimer, a transmembrane segment has a length of 1.5 to 2.5 nm.

The transmembrane segments of membrane-bound proteins are examples of transmembrane segments/moieties. Membrane-acting anti-microbial peptides and other natural products that have, for example, cylindrical- and tape-like amphiphilic structures are also examples of transmembrane segments/moieties. Examples of transmembrane segments (e.g., transmembrane moieties) also include, but are not limited to, alkyl moieties comprising 5 to 8 carbons (or 2 to 4 carbons for a transmembrane segment of a dimer) and transmembrane peptides (e.g., a structural component or motif of a transmembrane peptide that can interact with a cell membrane), transmembrane domains of proteins (e.g., transmembrane domains of proteins that have alpha-helical structure or beta-sheet structure), amphiphilic alpha-helices or beta-sheets that have both a hydrophobic and a hydrophilic side, and natural or synthetic cylindrical or tape-like amphiphilic structures such as, for example, derivatives of nystatin, amphotericin B, and alamethicin. For example, amphiphilic alpha-helical peptides are cynlindrical and beta-sheet peptides are tape-like. Examples of amphiphilic structures include, but are not limited to, oligoether chains such as, for example, oligo(butylene glycol), cylindrical (helical) and tape-like (sheet) amphiphilic peptides such as, for example, magainins and tachyplesins, antibiotic macrocyclic natural products such as, for example, the macrolide antibiotic amphotericin B.

A thermoresponsive segment is a moiety/group covalently bound to an end of the transmembrane segment that not covalently bound to the macrocyclic backbone (e.g., opposite or remote to a terminus of the transmembrane segment bound to the macrocyclic backbone). A thermoresponsive segment can have a thermoresponsive moiety. A thermoresponsive segment (e.g., thermoresponsive moiety) has features (e.g., structural features) or properties that are altered in different thermal environments. For example, a thermoresponsive segment or moiety convert from extended (hydrophilic) state to an ordered (compact, hydrophobic) state at a transition temperature. The thermoresponsive segments can be covalently bound to a transmembrane segment through various functional moieties. A thermoresponsive moiety can be covalently bound to a transmembrane segment through, for example, a thioether moiety (—S—), an amide moiety (—NC(O)—) moiety, or a triazole moiety. For example, a thermoresponsive segment can be covalently bound to the macrocyclic backbone through a moiety formed using click chemistry (e.g., photoclick chemistry). The thermoresponsive segment can include a linking moiety (e.g., an alkyl group) that connects a thermoresponsive moiety to the transmembrane segment (e.g., via a functional moiety) or the functional moiety that covalently connects the macrocyclic backbone to the transmembrane segment.

Examples of thermoresponsive segments (or thermoresponsive moieties) include, but are not limited to, thermoresponsive oligomers (e.g., NIPAM) and thermoresponsive peptides (e.g., elastin-like peptides). Examples of thermoresponsive segments (or thermoresponsive moieties) also include, but are not limited to, peptides/proteins comprising one or more pentapeptide repeat units (e.g., VPGVP (SEQ ID NO:1), VPGEG (SEQ ID NO:2), VPGKG (SEQ ID NO:3), and IPGVG (SEQ ID NO:4)) from thermoresponsive elastin-like peptides (ELPs). These pentapeptides can have different properties including different transition temperatures for their conversion from an extended (hydrophilic) state to an ordered (compact, hydrophobic) state. Other examples of thermoresponsive segments (or thermoresponsive moieties) include, but are not limited to, oligomers of gamma-amino acids and foldamers thereof, short (e.g., $M_w$ and/or $M_n$ of 1,000 to 5,000 g/mol, including all integer g/mol values and ranges therebetween) thermoresponsive polymers chains based on poly(N-isopropylacrylamide) (PNIPAM), and other thermo-responsive polymers such as, for example, poly[2-(dimethylamino)ethyl methacrylate] (pDMAEMA), hydroxypropylcellulose, poly(vinylcaprolactame), and polyvinyl methyl ether.

For example, macrocyclic compounds have the following structure:

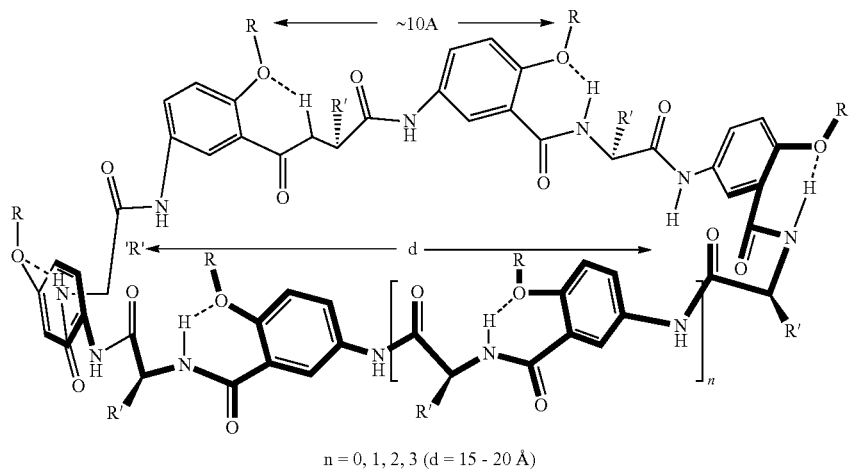

$n = 0, 1, 2, 3$ ($d = 15 - 20$ Å)

where R groups comprising a transmembrane moiety and, optionally a thermoresponsive moiety and R' groups are side-chains from alpha-amino acids. The side chains can be from one or more naturally occurring alpha-amino acids and/or one or more non-naturally occurring alpha amino acids. In various examples, the R' groups individually, at each occurrence in the macrocycle:

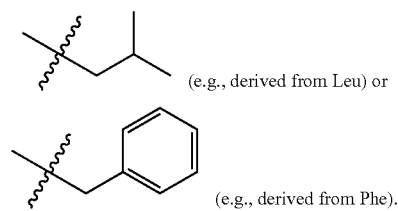

For example, in the example macrocycle structure above:

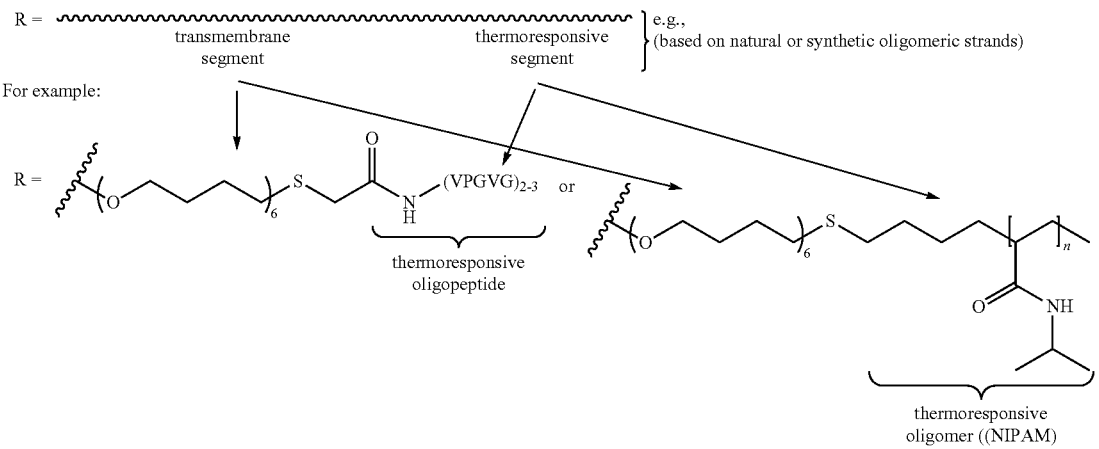

R' = side chain of (L or D) alpha-amino acid

In an example, the alpha-amino acid is not proline. In various examples, n in the thermoresponsive oligomer in R is 2 to 20, including all integer values and ranges therebetween. In various examples, the alkyl moiety of the transmembrane segment (or transmembrane moiety) of R in this example comprises 5 to 8 carbons and/or the thermoresponsive oligopeptide of the thermoresponsive segment (or thermoresponsive moiety) of R has various thermoresponsive amino acid sequences (optionally, the thermoresponsive segment of R various thermoresponsive groups (e.g., thermoresponsive oligomers). In various examples, one or more of the phenyl moieties of the macrocycle backbone are substituted in the position adjacent to the ether group (—O—R) group. Examples of substituent groups such as aliphatic groups, halide groups, ether groups, acid/ester groups, amine groups.

In various examples, a dimer, which can be referred to as a pore-forming compound or molecular channel-former, comprises two macrocyclic units (e.g., which can be macrocyclic groups derived from macrocyclic compounds of the present disclosure) disclosure covalently bound to each other through one or more covalent bonds that connect the bottoms of the two macrocyclic units (e.g., two crosslinked macrocyclic compounds of the present disclosure). The covalent bond(s) can be referred to as crosslinking bonds. A macrocyclic compound/unit has two openings one of which is smaller than the other. The bottom of a macrocyclic compound/unit corresponds to the narrower of the two openings of the macrocycle. The top of a macrocyclic compound/unit corresponds to the broader of the two openings of the macrocycle. These dimers can be referred to as bottom-to-bottom linked dimers, top-to-bottom linked dimers, or top-to-top linked dimers. In various examples, the dimer comprises two macrocyclic units of the present disclosure, where the bottoms of the two macrocyclic compounds, the top of one macrocyclic unit and bottom of a second macrocyclic unit, or the tops of two macrocyclic units are covalently bound to each other by, for example, one or more disulfide bonds, one or more aliphatic groups, or more triazole groups, or a combination thereof. In various examples, the dimer comprises two macrocyclic units/compounds of the present disclosure, where the bottoms of the two macrocyclic units/compounds, the top of one macrocyclic unit/compound and bottom of a second macrocyclic/unit compound, or the tops of two macrocyclic units/compounds are covalently bound to each other by, for example, one or more crosslinking moieties that are covalently bound to the macrocyclic core via one or more disulfide bonds, one or more aliphatic groups, or more triazole groups, or a combination thereof. In various examples, a dimer is formed using click chemistry (e.g., photoclick chemistry) or olefin metathesis. Examples of dimers are shown in FIG. 15.

In an example, a dimer is formed from two macrocyclic units having the following structure:

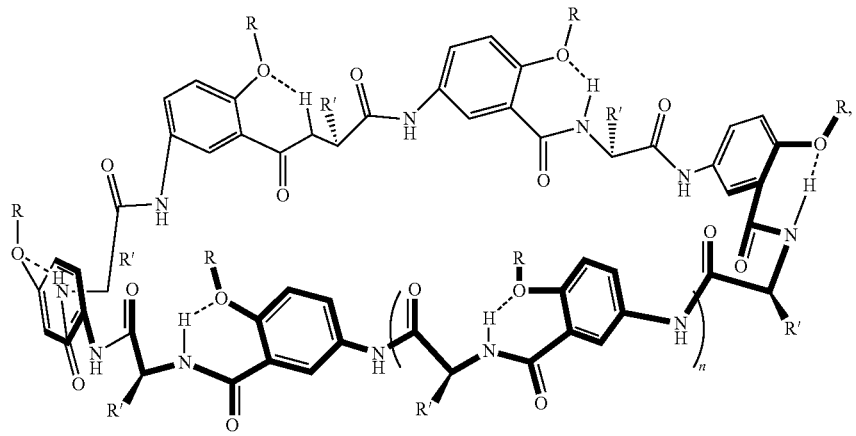

where R at each occurrence in the macrocyclic unit is a group comprising a transmembrane segment-thermoresponsive segment moiety or a crosslinking moiety;

R' is a side chain of an alpha amino acid as described herein, and optionally, one or more of the phenyl rings is substituted as described herein (e.g., at the position adjacent to the ether group (—O—R) group with a group independently at each occurrence in the macrocyclic compound selected from the group consisting of aliphatic groups, halide groups, ether groups, acid groups, ester groups, and amine groups); and n is 0, 1, 2, or 3, where at least one of the R groups is a crosslinking moiety and the two macrocyclic compounds are joined by at least one crosslinking moiety.

The macrocyclic units of the dimers are joined (e.g., covalently linked) by crosslinked by crosslinking moieties. A crosslinking moiety can be referred to as a tether. Non-limiting examples of crosslinking moieties include thermoresponsive crosslinking moieties (e.g., thermoresponsive crosslinking moieties comprising a thermoresponsive segment such as, for example, thermoresponsive segments described herein) and photoresponsive crosslinking moieties (e.g., photoresponsive crosslinking moieties comprising a photoresponsive moiety such as, for example, an azobenzene moiety or thioindogo moiety). A photoresponsive moiety undergoes a light-modulated conformational change. For example, an azobenzene moiety adopts cis conformation when being irradiated by light of ~380 nm, and adopts the trans conformation when being irradiated by light of ~500 nm. The thioindigo group adopts trans conformation when being irradiated with light of ~450 nm and cis conformation when being irradiated with light of ~550 nm. When incorporated into a macrocyclic dimer, the light-triggered conformational conversion of the photo-responsive moiety in turn results in the conformational change of the dimer, which controllably turns a transmembrane pore formed by a dimer on (open) or off (closed).

The crosslinking moieties can be joined to the macrocycles by various linking moieties. Examples of linking moieties are known in the art and are provided herein. Subjecting a dimer with one or more thermoresponsive crosslinker and/or one or more photoresponsive crosslinker to an appropriate external stimulus (e.g., a specific temperature change or specific wavelength of electromagnetic radiation (light), respectively) triggers a conformational change of the dimer.

Figure 8A:
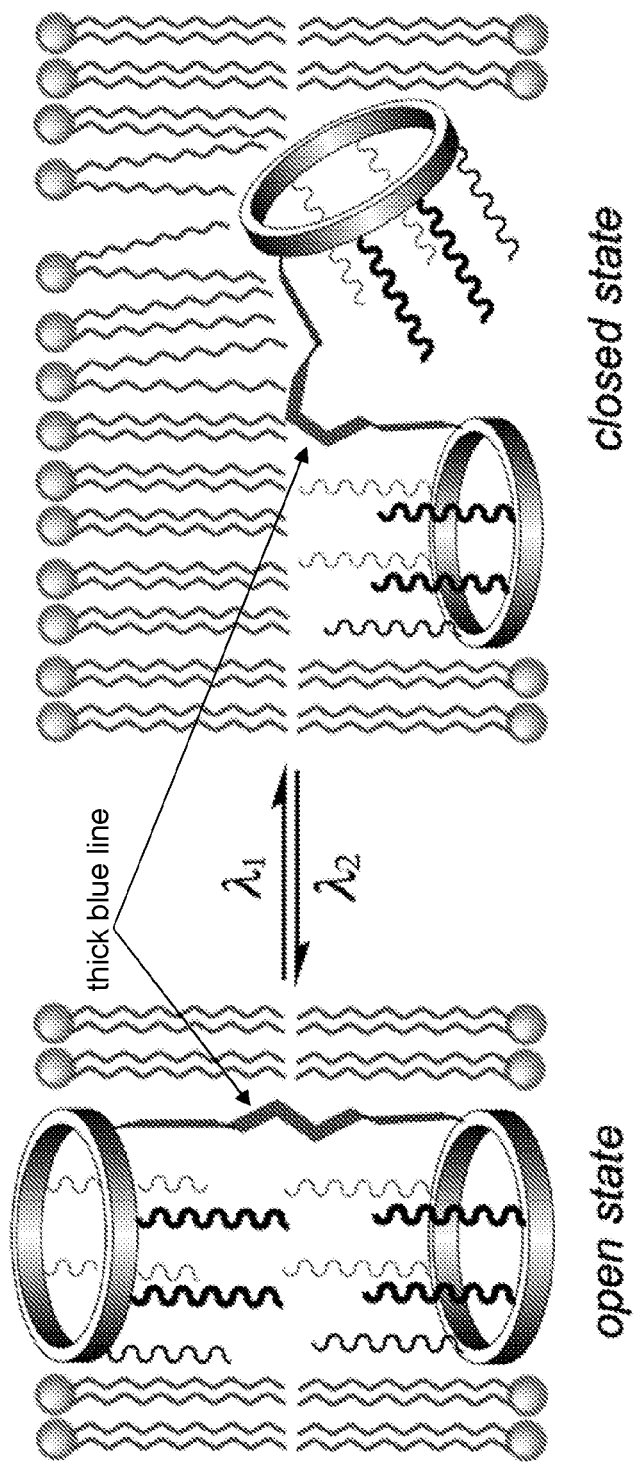
FIGS. 8A and 8B show a design of a photo-responsive unimolecular transmembrane pore (FIG. 8A) and a thermoresponsive unimolecular transmembrane pore (FIG. 8B). The unimolecular structure consists of two macrocyclic portals, a covalent tether and multiple membrane-compatible chains or tentacles (wiggle lines).

An example of a dimer with a photoresponsive crosslinker is shown in FIG. 8A. A covalent linker (tether) connecting two macrocyclic portals (macrocyclic units) contains a photoresponsive moiety (thick blue line) that undergoes conformational change upon being irradiated with light of different wavelengths, changing the overall conformations of the pore-forming structure and leading to open and closing of the transmembrane pore. In an example, a dimer is a reversibly switchable, light-responsive dimer or unimolecular pore former.

Figure 8B:
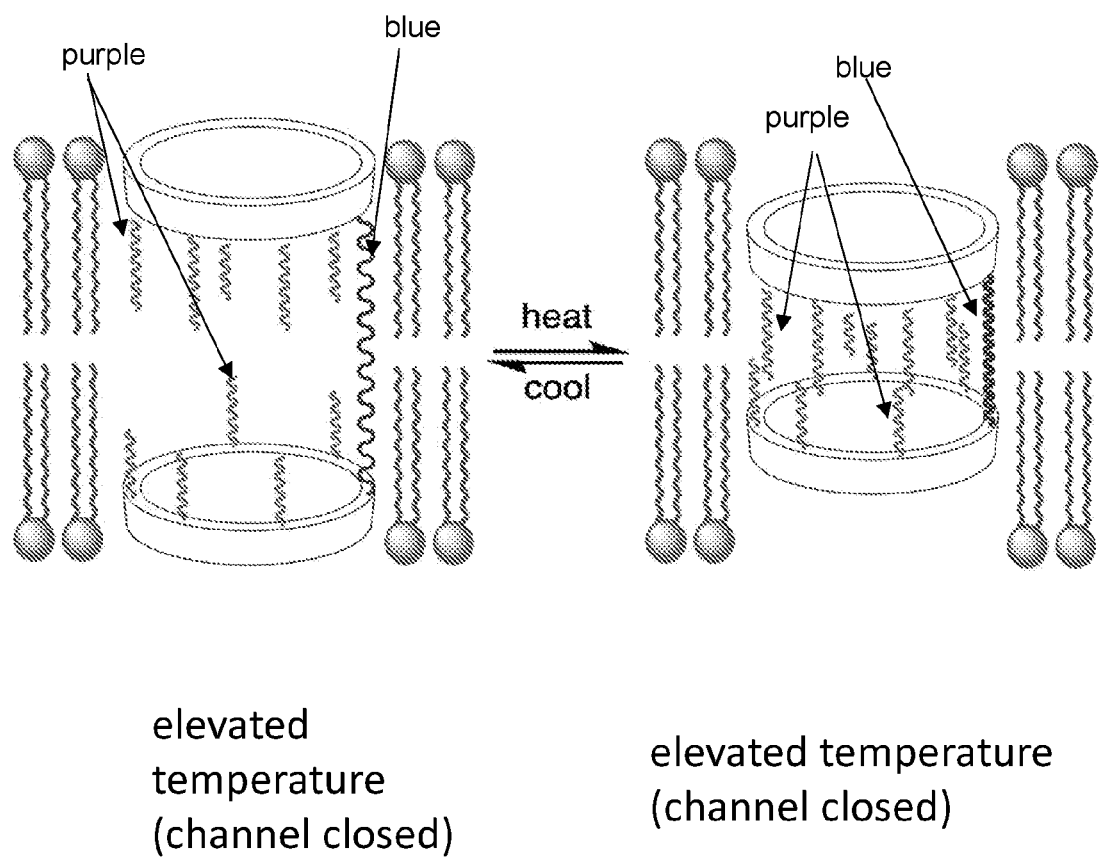

An example of a dimer with a thermoresponsive crosslinker is shown in FIG. 8B. A covalent linker (blue) connecting two macrocyclic portals (macrocyclic units) is temperature (thermo)-responsive and undergoes conformational conversion as temperature changes, which alters the overall lengths of the pore-forming structure and leading to open and closing of the transmembrane pore.

In an example, macrocyclic compounds or dimers comprise alpha-amino acid residues bearing side chains with reactive groups capable of engaging in reversibly forming covalent bonds such as disulfide, olefin (e.g., via olefin metathesis), ester, imine, and hydrazone bonds. Reactive groups that irreversibly form covalent linkages can also be introduced into the alpha-amino residues if the dimerization reaction is performed under high-dilution conditions. For example, two types of macrocyclic compounds that have alpha-amino residues carrying side chains amino and carboxyl groups can be crosslinked by irreversibly forming amide bonds under high-dilution condition in the presence of a coupling reagent.

A macrocyclic compound or dimer (e.g., a macrocyclic unit) can have various diameters. For example, a macrocyclic compound or dimer has a diameter of 15 to 20 angstroms. A macrocyclic compound or dimer can have an inter-transmembrane group/transmembrane group-thermoresponsive group distance of about 10 angstroms.

The macrocyclic compounds and dimers of the present disclosure can be referred to as pore-forming compounds. When contacted with a cell (plasma) membrane the macrocyclic compounds or dimers can form a pore (e.g., pore structure) in the cell membrane that provides fluid contact between the extracelluar space and intracellular space. Pores formed by the pore-forming compounds on, partially within, or within the plasma membrane serve as "doors" that allow the controllable release of a cargo (e.g., hydrophilic therapeutic agents (e.g., drugs) and cell-protective agents (e.g., cryoprotectants) that may be encapsulated inside vesicles (liposomes). In various examples, the drugs and cell-protective reagents are hydrophilic drugs that cannot penetrate the cell membranes.

Macrocyclic compounds or dimers can exist in an open configuration (e.g., at about 5° C.) and a closed configuration (e.g., at body temperature (such as, for example, 37° C.). Without intending to be bound by any particular theory, it is considered that the conformational change of the thermoresponsive segments (i.e., the thermoresponsive segments become compact and hydrophobic) at elevated temperature and aggregate together, seals off the transmembrane pore. The macrocycle (compound or dimer unit(s)) can move from an open configuration to a closed configuration in response to a change in the temperature of the environment in which macrocycle is present. An example of an open configuration and a closed configuration and temperature response of a macrocycle are provided in FIG. 1.

Macrocyclic compounds or dimers can comprise additional compounds (cargo) in the interior space defined by the tentacles in the closed configuration. For example, a macrocycle comprises one or more additional compound. Examples of additional compounds include drugs, imaging agents, and the like.

In an aspect, the present disclosure provides compositions comprising one or more macrocyclic compound and/or one or more dimer of the present disclosure. For example, a composition comprising one or more macrocyclic compound and/or one or more dimer (e.g., pore-forming compound) of the present disclosure can be used in a method of cryopreservation.

For example, a composition is an aqueous solution comprising one or more macrocyclic compounds and/or one or more dimers of the present disclosure. The composition may be a buffer. The composition may further comprise one or more CPAs, ions, nutrients typically used in cell or tissue culture, or a combination thereof. Examples of suitable CPAs, ions, and nutrients are known in the art.

Figure 10:
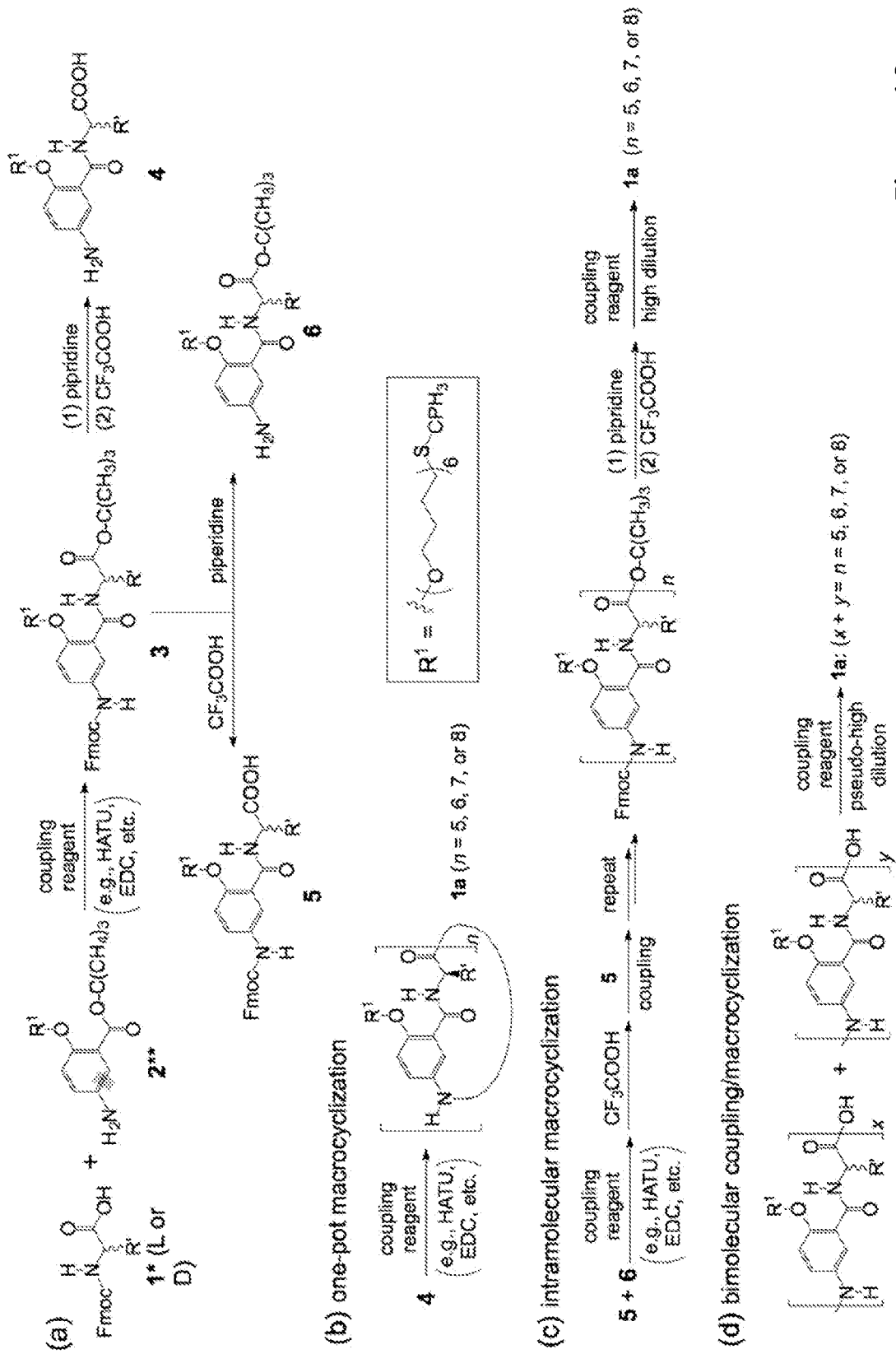
FIG. 10 provides an example of a macrocyclic compound synthesis scheme.

In an aspect, the present disclosure provides methods of making macrocyclic compounds and dimers of the present disclosure. For example, it is expected that macrocyclic compounds of the present disclosure can be made according to the reaction scheme shown in FIG. 10.

Figure 11:
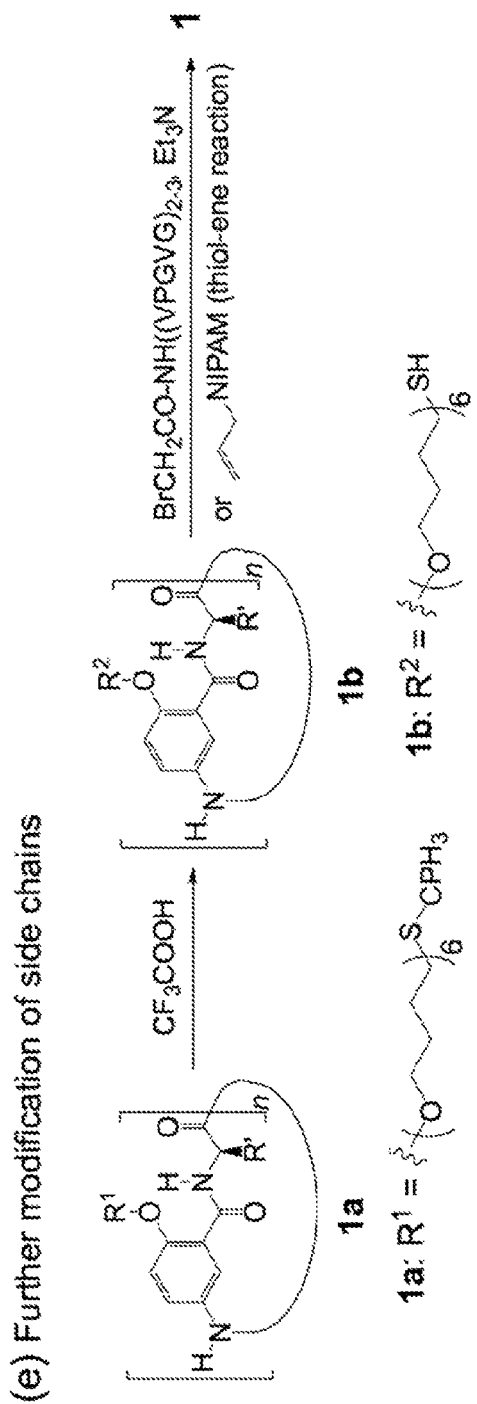
FIG. 11 provides an example of a side-chain ("tentacle") synthesis scheme.

Various side chains (tentacles) comprising a transmembrane segment and, optionally, a thermoresponsive segment can be synthesized. For example, a side chain can be synthesized according to FIG. 11.

In an aspect, the present disclosure provides uses of macrocyclic compounds, dimers, and compositions of the present disclosure. For example, macrocyclic compounds and dimers can be used in cryopreservation methods, methods of delivering (e.g., controlled/selective delivery) or release of drugs, nutrients, imaging agents, radioactive or fluorescent tracers, or a combination thereof, as membrane-bond sensor molecules and ions (e.g., in methods for detecting chemical or biological warfare-like toxic proteins and bacteria such as, for example, anthrax), as nano-containers for catalyzing chemical reactions, and as arrays (membranes) of nanopores (which can be used as, for example, materials for or in methods of separation and purification of, for example, molecules and ions).

For example, macrocyclic compounds or dimers of the present disclosure can be used for delivery of cargos (e.g., cryoprotectant agents (CPAs)). Macrocyclic compounds and dimers of the present disclosure provide a fundamentally different approach to cargo (e.g., CPA delivery). The macrocyclic compounds and dimers are expected to prevent ice formation by facilitating transport of CPAs into cells. Macrocyclic compounds and dimers are expected to form biomimetic nanopores that can function as cargo (e.g., CPA) transmembrane "mega highways" to facilitate safe and efficient intracellular delivery and removal of cargos (e.g., CPAs during cryopreservation). These rationally designed synthetic nanopores are expected to serve as selective transmembrane channels to transport cargos. For example, these rationally designed synthetic nanopores are expected to serve as selective transmembrane channels to transport CPAs when protein channels typically malfunction at <3° C. As a result, the cell's CPA exposure time to reach ice-free cryopreservation temperature can be reduced significantly. Post-preservation cell yield and viability will be greatly improved by reducing intracellular ice formation.

Figure 12:
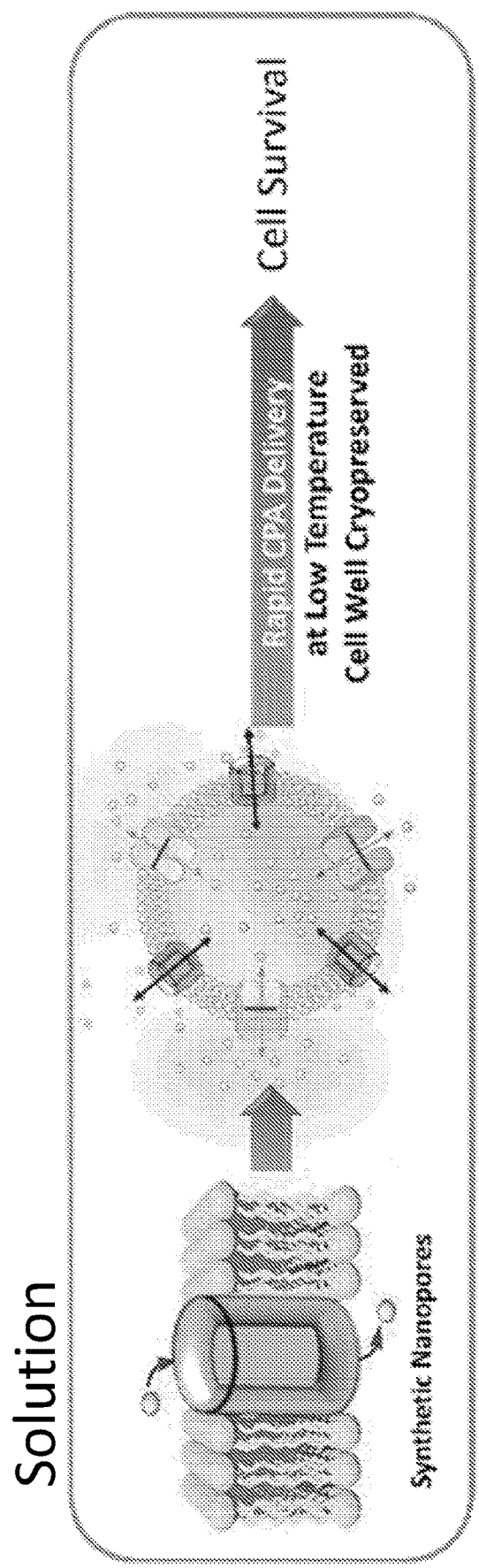
FIG. 12 shows a graphical representation of a method of CPA delivery.

Macrocyclic compounds and dimers of the present disclosure are expected to facilitate the intracellular delivery and transmembrane equilibration of cargos (e.g., CPAs). Size and function tunable, temperature-responsive synthetic nanopores comprising one or more macrocycle of the present disclosure are expected to serve as a "mega highway", which remain open at subzero temperature to effectively deliver cargos (e.g., CPAs) across the cell membrane. In the case where the cargo is a CPA, this will allow a significant decrease in both the CPA exposure time and loading/unloading temperature during freezing. This temperature-responsive feature, or other engineered environmentally sensitive stimuli, will allow synthetic nanopores to seal off at or above physiological temperature, which offers minimum interference of membrane integrity and low toxicity. This method is expected to be effective when CPA loading in tissues using the "liquidus tracking" or step-wise methods where increasingly concentrated solutions of CPA are loaded in the tissue/organ at progressively decreasing temperatures. A graphical representation of a method of CPA delivery is shown in FIG. 12

In an example, one or more macrocyclic compounds and/or one or more dimers of the present disclosure (which can form synthetic nanopores comprising one or more macrocyclic compounds of the present disclosure) or a composition of the present disclosure are delivered (e.g., administered) into a target system (such as for example, an organ, tissue, or individual (e.g., a mammalian organ or tissue and mammals and non-human mammals)). Methods of administration are known in the art.

Figure 2:
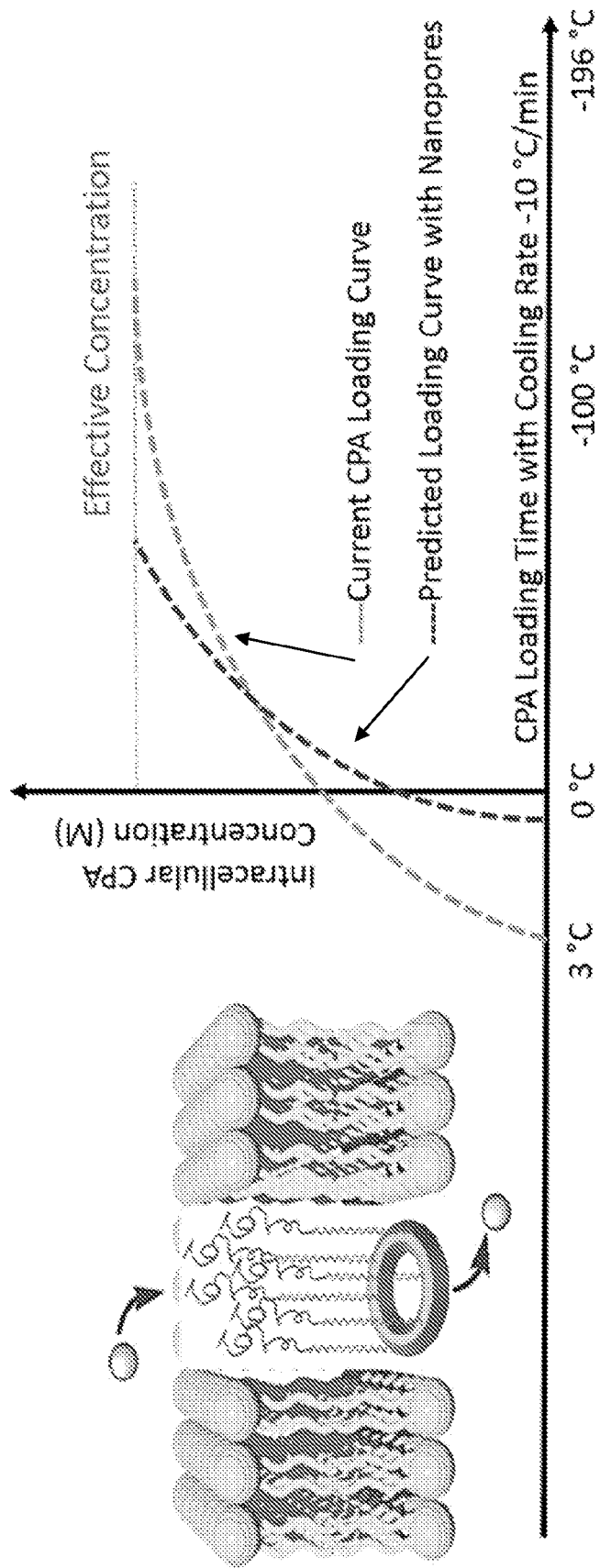
FIG. 2 shows CPA loading via incorporation of nanopores, resulting in 50% less time required to reach effective intracellular concentration compared to current methods using high osmotic pressure.

In an example, one or more macrocyclic compounds and dimers of the present disclosure (which can form synthetic nanopores comprising one or more macrocyclic compounds of the present disclosure) are delivered into a target system (such as for example, an organ or tissue (e.g., a mammalian organ or tissue)) at a physiological temperature (e.g., 37° C.), followed by CPA loading at hypothermic temperature (e.g. <4° C.). A high influx rate of CPAs through shape-persistent nanopores can be maintained during cooling as a function of the concentration gradient across cell membrane, thereby reducing the required time to reach vitrification concentrations. Upon rewarming, the synthetic nanopores are expected to facilitate rapid removal of CPAs to reduce exposure time and the consequent toxic side effects. At or above physiological temperature, the nanopores will seal off, and can be washed out from the system resulting in low toxicity. This use of synthetic nanopores can significantly reduce toxicity and cell injury (e.g., FIG. 2) due to osmotic shrinkage caused by CPAs and salt during both the cooling and rewarming processes via (1) reducing CPA exposure time and (2) enabling rapid CPA loading and unloading at lower temperatures.

Moreover, versatile functional organic nanotubes of diverse sizes and properties by modifying inner macrocyclic cavities allow selective CPA transport while preventing ion exchange. Incorporation of functional supramolecular assemblies to enhance membrane permeability of CPAs could lead to a revolutionary solution to long-term cryopreserve large/complex tissues/organs, which will potentially enable "Organs on Demand."

Cryoprotective agents (CPAs) are additives that improve the post-thaw viability of cryopreserved biological systems from cells to large and complex tissues/organs by preventing ice crystal nucleation and growth. Membrane permeable CPAs also prevent osmotic shrinkage of the cells and reduce the volume of available water by penetrating and equilibrating across the cell membrane. All known CPAs exhibit various levels of cytotoxicity at effective concentration which may be decreased by reducing the CPA loading temperature and exposure time. However, most CPAs become effectively impermeable at sub-zero temperatures.

The steps of the methods described in the various examples disclosed herein are sufficient to carry out the methods of the present disclosure. Thus, in an example, a method consists essentially of a combination of the steps of the methods disclosed herein. In another embodiment, a method consists of such steps.

The following example is presented to illustrate the present disclosure. The example is not intended to limiting in any matter.

Example 1

This example provides a description of a use of the macrocyclic compounds of the present disclosure in a cryopreservation method.

A design for cryopreservation involves, the preparation of bouquet-like molecular channel-formers (e.g., macrocyclic compounds of the present disclosure) that include a macrocyclic template to which multiple tentacles containing membrane spanning (purple) and temperature-responsive terminal (blue) segments are attached (FIG. 1).

Molecular simulation indicated that, for the passage of glucose through the cylindrical cavity of the tubular transmembrane an internal van der Waals pore diameter of >9 Å is required. Disaccharide passage requires a pore size of 13 Å respectively. Energy-minimization revealed that the macrocyclic template (FIG. 1) can consist of six basic units, each of which contains an α-amino acid and aromatic m-amino acid residue. Such a macrocycle has an overall rigid (non-deformable) shape with an inner cavity of ~17 Å across for sufficient mono-, di-saccharides transport. The multiple (R) sites of the cyclic template allow the attachment and parallel arrangement of tentacles. The α-amino acid residues can be based on leucine (Leu) or phenyalanine (Phe), which introduce (R') side chains that serve to facilitate the membrane compatibility and adjust other properties of molecular bouquets.

Each of the tentacles (FIG. 1) is composed of two segments, an oligoether segment that is known to be able to span lipid bilayers and a temperature-responsive oligopeptide segment having two repeats of the sequence VPGVG (SEQ ID NO:5) that occurs in mammalian elastin. Study of short elastin-like peptides (ELPs) containing one to five repeats of the VPGVG (SEQ ID NO:5) sequence revealed that these short peptides, along with their high molecular weight polymeric analogs, adopt a flexible (random coil) conformation in water at temperatures below 37° C. Short ELPs with as few as one VPGVG (SEQ ID NO:5) unit undergo a reversible transition from an extended, hydrophilic state to a compact, rigid, and hydrophobic conformation as temperature increases.

In the molecular bouquet (FIG. 1), at low temperature, the peptide segments of the tentacles are hydrophilic random coils that are solubilized in aqueous (extracellular) media and therefore do not block the pore. As a result, a barrel-like structure that contains a cylindrical inner pore with a diameter defined by the cyclic template results (FIG. 1). The molecular bouquet will serve as a transmembrane pore allowing CPAs such as mono- and disaccharides to be transported. At elevated temperatures, the peptide segments will adopt a compact, rigid conformation and also become hydrophobic. As a result, the peptide segments will undergo intramolecular aggregation that is driven by hydrophobic interaction, which block the channel and prevent the transport of CPAs and other molecules to prevent warm toxicity.

Example 2

This example provides a description of macrocyclic compounds of the present disclosure and use thereof.

Figure 3:
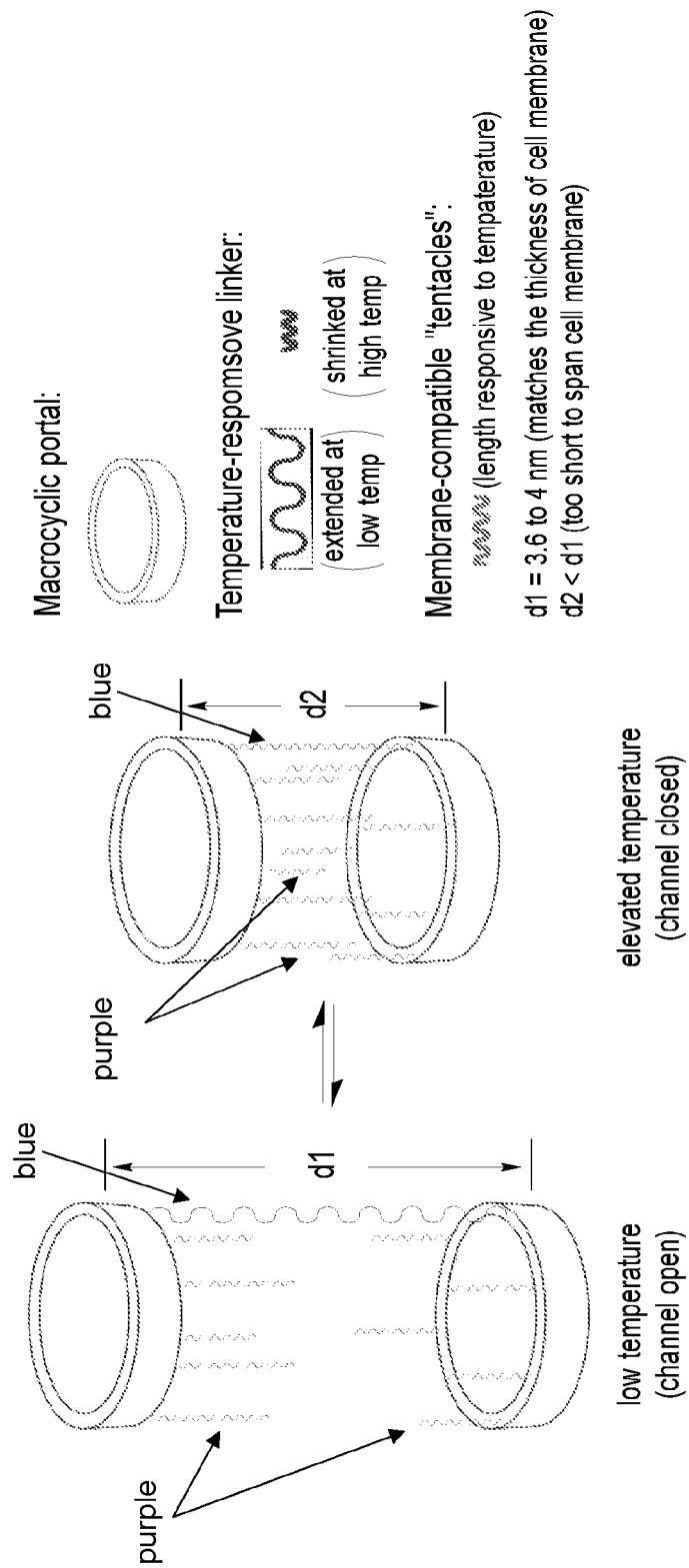
FIG. 3 shows a schematic illustration of a dimer of the present disclosure, which is a molecular channel-former with two macrocyclic portals connected via a temperature-responsive linker (blue). Membrane-compatible chains (or tentacles, in purple) are attached to the rigid macrocyclic portals to facilitate channel formation and transport of molecules or ions.

General design, shown in the FIG. 3, involves pore- or channel forming molecule consisting of two macrocyclic portals connected via a temperature-responsive linker (blue) to which multiple tentacles (purple) that are compatible to cell membranes spanning are attached. At a low temperature (e.g., 0-4° C.), the temperature responsive linker will be extended, with a length that allow the two portals to stay need the two surfaces of a lipid bilayer, leading to an opening channel. At an elevated temperature (e.g., 37° C.), the temperature-responsive linker will adopt a shrunk (compact) conformation, which shortens the distance between the two portals, leading to a closed channel. The tentacles will serve to form a channel with a pore size that is roughly defined by the macrocyclic portals.

Materials. Three macrocyclic portals (FIG. 4) consists of 6-8 basic units, each of which contains an α-amino acid and aromatic m-amino acid residue, with inner diameters ranging from ~1.8 nm to 2.4 nm.

Figure 4:
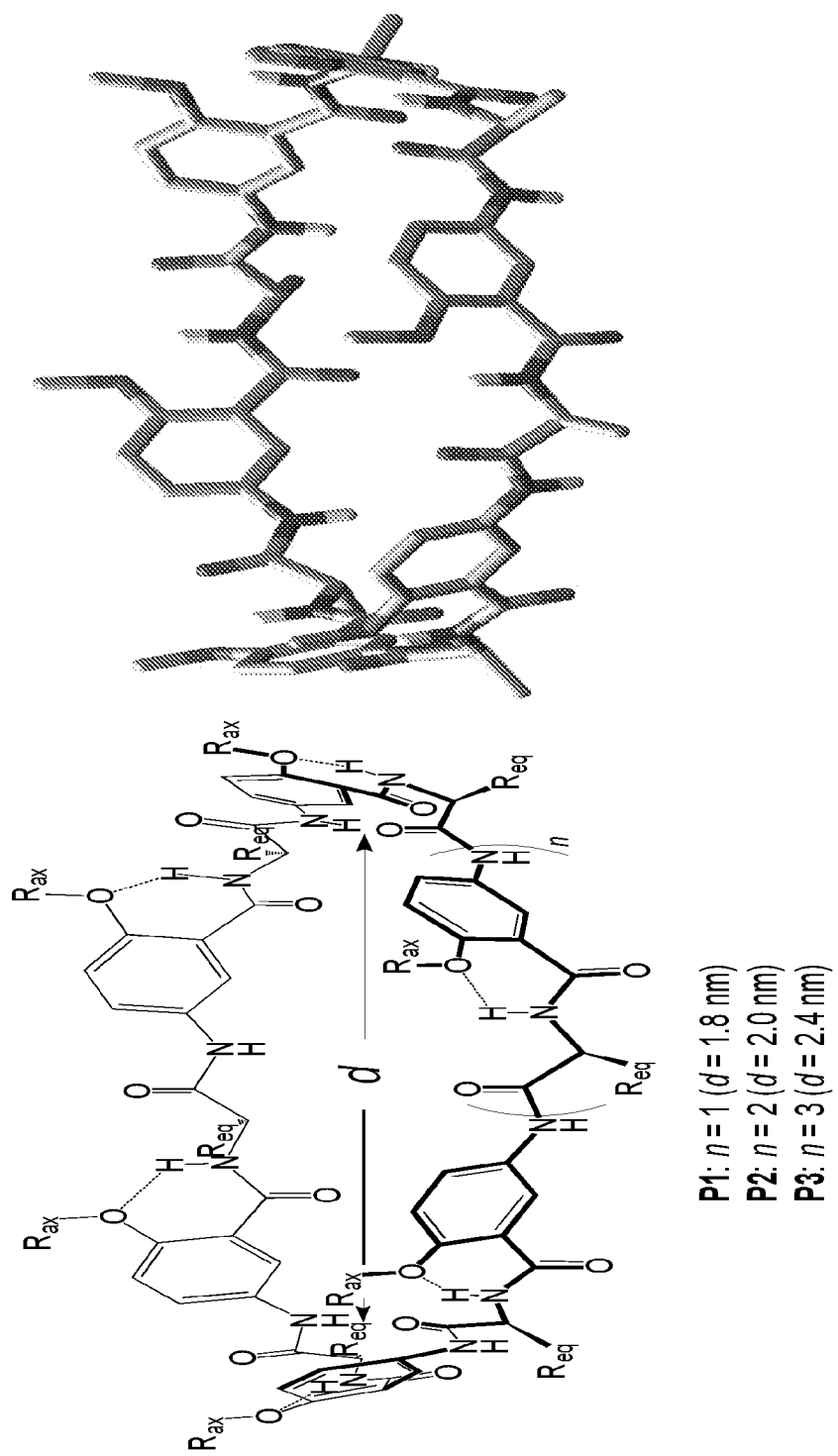
FIG. 4 shows structural designs of macrocyclic portals (left) with the energy-minimized conformation of P1 (right) shown.

The specific structures shown of macrocycles P1-P3 serve as the cyclic portals. Based on a hybrid peptide backbone consisting of alternating α-amino acid and aromatic m-amino acid residues, the backbones of P1-P3 are overall rigid and offer defined lumen of ~1.8, 2.0, and 2.4 nm across, as revealed by the computed (energy-minimized) conformations of these macrocycles (FIG. 4). The lumen of P1-P3 should allow the passage of a variety of molecules such as mono-, di-, and oligosaccharides. Macrocycles P1-P3 also carry axially oriented side chains ($R_{ax}$) that provide multiple sites for attaching the covalent tether and the membrane-contacting tentacles. Another set of equatorially oriented side chains ($R_{eq}$), i.e., those of the α-amino acid resides, offer additional structural tunability.

The membrane-contacting tentacles (FIG. 3, purple chains) are based on oligoether chains that are known to be able to span lipid bilayers and also facilitate the transmembrane transport of polar molecules and ions (FIG. 5). Other chain-, rod-, tape-like, or cylindrical-shaped amphiphilic structural units such as extended or alpha-helical peptides, also serve as membrane-compatible tentacles. The length of the tentacles is about 12 Å, which, along with each portal to which they attach, can span about half of a lipid bilayer.

The temperature-responsive linker (FIG. 3, blue chain) is based on oligopeptides or polymer chains that are well known to have tunable and predictable thermo-responsive behavior (FIG. 6). The linker, HS-ELP-SH or HS-NIPAM-SH, is designed to be symmetrical and carries two terminal thiol groups, to facilitate synthesis. Unsymmetrical peptide or polymer chains can also be adopted. Temperature-responsive oligopeptides such as those having 2-5 repeats of the sequence VPGVG (SEQ ID NO:5), which occur in mammalian elastin are well known to adopt a flexible (extended random coil) conformation in water at temperatures below 37° C. Oligomers consisting of the VPGVG (SEQ ID NO:5) unit undergo a reversible transition from an extended, hydrophilic state to a compact, rigid, and hydrophobic conformation as temperature increases. Well studied thermo-responsive polymer chains such as, but not limited to, poly(N-isopropylacrylamide) (NIPAM), can also be incorporated similarly. The temperature-dependent conformation change of the linker results in change in the distance between the two portals, leading to the opening of transmembrane channel at low temperature and the closing of the channel at elevated temperature.

Methods. Synthesis of unimolecular pore-formers. The macrocyclic portals are based on the unknown P1-P3, which share their backbone with a class of well-established hybrid peptides that were developed by the PI's group as information-storing H-bonded duplexes. The uncyclized oligomeric precursors of the macrocyclic portals will be synthesized based on known method[7] and will then be subjected to intramolecular cyclization to give macrocycles P1-P3. An example of a synthesis of unimolecular pore-formers is shown in FIG. 13.

Figure 13:
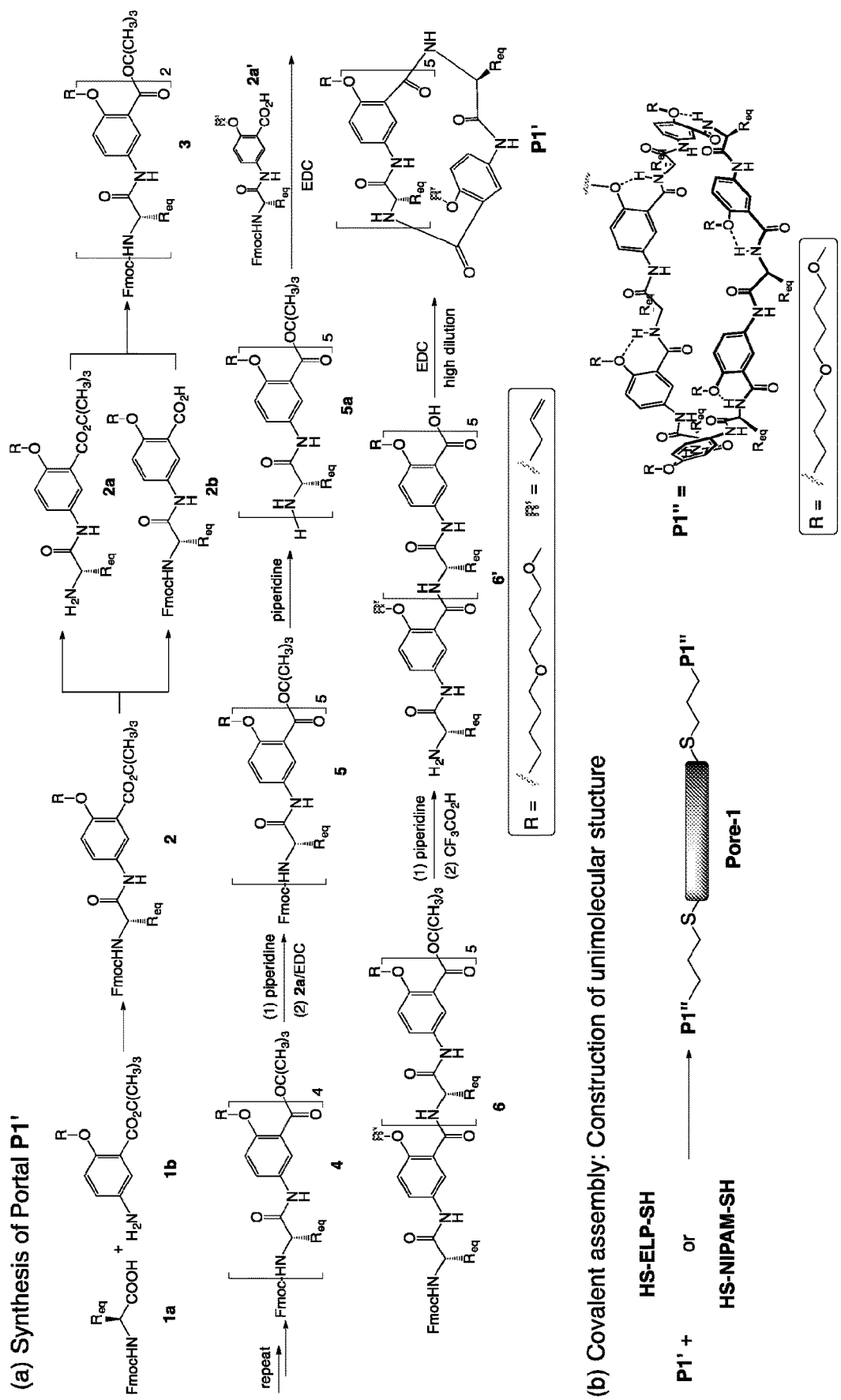
FIG. 13 provides an example of a synthesis of unimolecular pore-formers.

The synthesis of P1', corresponding to P1 and the final product Pore 1, are presented in FIG. 13. The synthesis of the other two portals derived from P2 and P3 follows the same steps. Coupling 1a and 1b leads to 2, which, after removing the Fmoc and t-butyl groups, gives amine 2a and acid 2b that are coupled to give 3. Subjecting 3 to the same deprotection/coupling steps results in 4, which, upon removing its Fmoc group and then couple with acid 2a, gives oligomer 5. Converting 5 into 5a followed by coupling with acid 2a' results in oligomer 6 that carries five identical di(butylene glycol) side chains R, and one side chain (R') bearing a propargyl group. Removing the Fmoc and t-butyl groups of 6 affords 6' which will be cyclized under high-dilution condition into macrocycle P1'. Tether T will be synthesized based on simple amide coupling of the corresponding 2-methoxyazidobenzoic acid with the commercially available 4, 4'-diaminoazobene. The covalent assembly of P1' (two equivalents) and linker HS-ELP-SH or HS-NIPAM-SH (one equivalent) into the final product Pore 1 will be achieved with the highly efficient, nearly quantitative "click" reaction between the allyl groups of P1' and the thiol groups of HS-ELP-SH or HS-NIPAM-SH.

Figure 7:
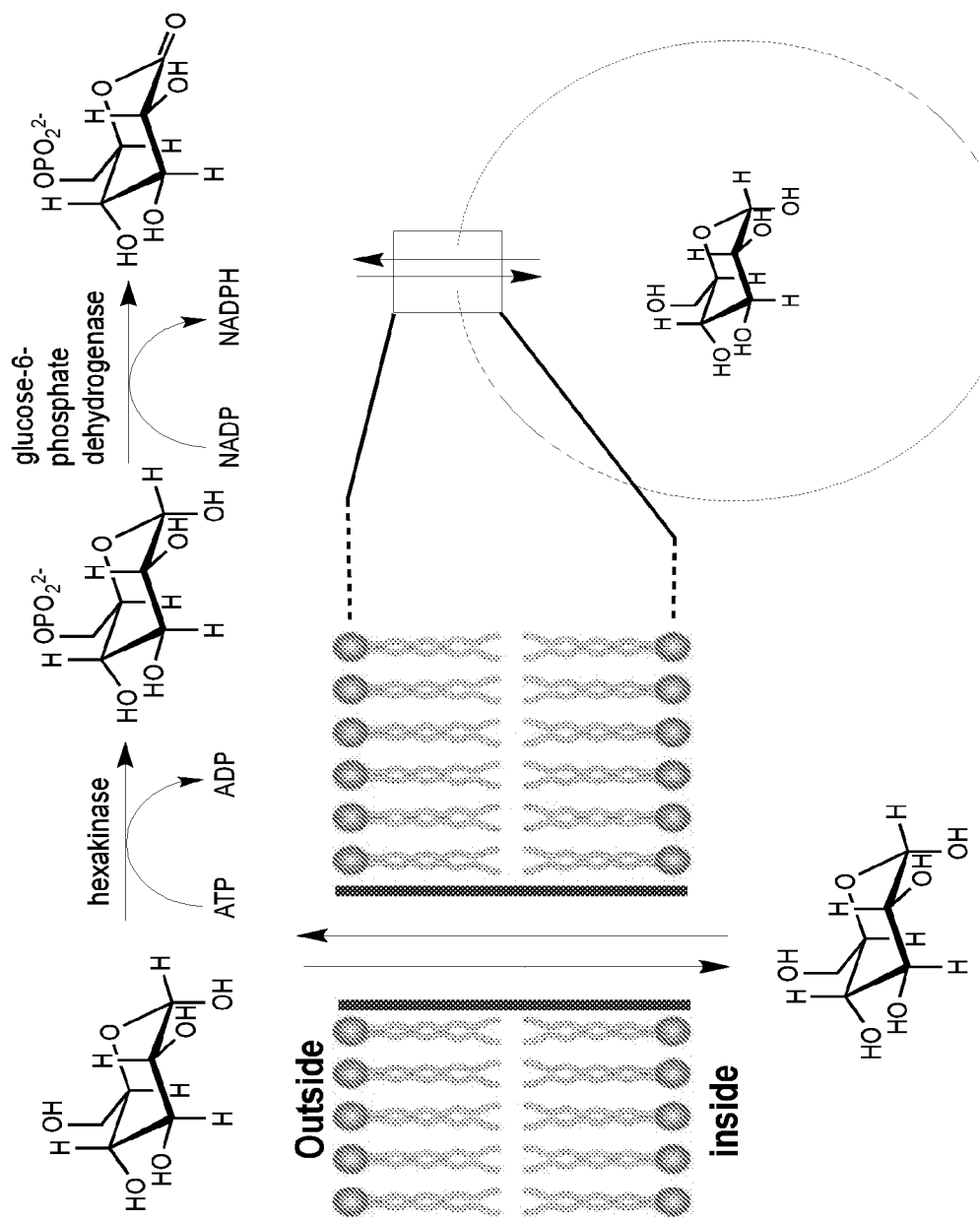
FIG. 7 shows a schematic illustration of channel-mediated glucose transport and the enzyme-coupled assay for monitoring the transport activity. Formation of the transmembrane pore structure(s) initiates glucose efflux from the liposome, which can be directly monitored by measuring the rate of NADPH production. The enzymes and cofactors employed are hydrophilic and thus cannot pass through the lipid membrane and are too large to penetrate the channel structure. Therefore, only the released glucose can undergo the enzymatic reaction.

Assessment of channel-mediated transport of membrane-impermeable compounds. The ability of Pore 1, Pore 2 and Pore 3 to mediate the transport of hydrophilic compounds such as various hydrophilic drugs and cryoprotectant agents (CPAs) across lipid bilayers can be evaluated at both low (~0° C.) and high (37° C.) temperatures using glucose as a model. Following reported procedures, glucose transport activity is studied in isotonic solutions (in 100 mM NaCl and 50 mM Tris buffer, pH 7.5) using glucose-entrapped large unilamellar lipid vesicles (LUVs) with ~150 nm in diameter. The transport phenomenon is monitored spectrophotometrically at 340 nm for the production of NADPH using an enzyme-coupled assay (FIG. 7). The kinetics of glucose transport is followed after the addition of various amounts of 3 to the glucose-entrapped liposomes at different initial glucose concentrations (e.g., 200, 150, 100, and 50 mM) (FIG. 7). A linear relation between transport rate and glucose concentration, consistent with a simple transmembrane channel-mediated diffusion process, exists. Assays are performed at near 0° C. and 37° C., respectively. The presence of a pore-former results in very different glucose transport activities, with efficient transport being observed at near 0° C. and drastically reduced or completely blocked transport at 37° C.

Example 3

This example provides a description of macrocyclic compounds of the present disclosure and use thereof.

The porating membranes of the present disclosure are important because of one or more of the following: (1) they are the first set of unimolecular pores with diameters comparable to those of protein pores but with much smaller masses, our system addresses a central challenge in the development of large synthetic pores; (2) the unimolecular nature, modest masses, and reversible switchability of our pores overcome many of the problems of known porating techniques, opening up new possibilities such as the controlled release or delivery of therapeutic or protective species encapsulated inside vesicles, for problems and challenges that are related to controlled membrane poration; or (4) the use of our pores requires no specialized equipment, no addition or removal of molecular or ionic species, and will be practically useful to large populations of cells. The porating membranes of the present disclosure are expected to demonstrate the feasibility of controlling transmembrane flux of molecules while maintaining cell viability.

Our approach is innovative in four aspects. First, the approach, based on uniquely switchable synthetic pores with large diameters, is expected to provide a hitherto unavailable technical opportunity that will widely useful for an array of biomedical problems that call for controlled, reversible poration of cells. Second, the structures provide a new series of transmembrane pores, which open and close based on light-triggered reversible conformational changes, for the controlled transport of impermeant hydrophilic molecules and thus the reversible permeation of membrane. Light-mediated gating of large molecular-transporting pores is desirable. Third, the modular nature of the synthetic strategy, which directly addresses a central challenge facing the synthetic field, i.e., the dearth of general strategies for preparing molecular architectures with lengths and diameters comparable to protein pores, will not only allow the rapid assembly of the pore-formers, but more importantly, will overcome the other two obstacles by quickly adjusting the membrane compatibility and light-responsiveness of the pore-formers based on the feedbacks from membrane-permeabilization experiments. Besides, the synthetic nature of our molecular pores means that a wide variety of structural and functional motifs beyond those offered by biological structures can be incorporated, which will greatly enhance the structurally and functionally diversity of transmembrane pores. The development of the unimolecular pores described herein are expected to provide new, powerfully enabling tools for research and applications based on the reversible poration of plasma membranes. The light-switchable nature of our system overcomes many of the major or even lethal problems encountered with known porating techniques by permitting the exchange of molecules across cell membranes while maintain cell viability.

Reversible membrane-permeabilization with transmembrane pores. General Design: Reversibly switchable, light-responsive unimolecular pores. The present examples a class of membrane-spanning, light-responsive unimolecular pores (FIG. 8A), which are expected to provide reversible membrane permeabilization that consist of three parts. The first are two macrocyclic portals, with an overall rigid backbones and a large lumen, sit at opposite sides of the lipid bilayer. The second module, a covalent tether, defines the membrane-spanning length of the pore. A photo-isomerizable moiety (thick blue line) in the tether undergoes cis-trans conformational change with light of different wavelengths and results in overall conformational changes that turn the unimolecular pore on or off. Multiple parallel chains or "tentacles" (wiggle lines) attached to the macrocyclic portals constitute the third structural units, which, along with the two portals, delineate the size, membrane-compatibility, and transporting capability of the transmembrane pore.

Figure 9:
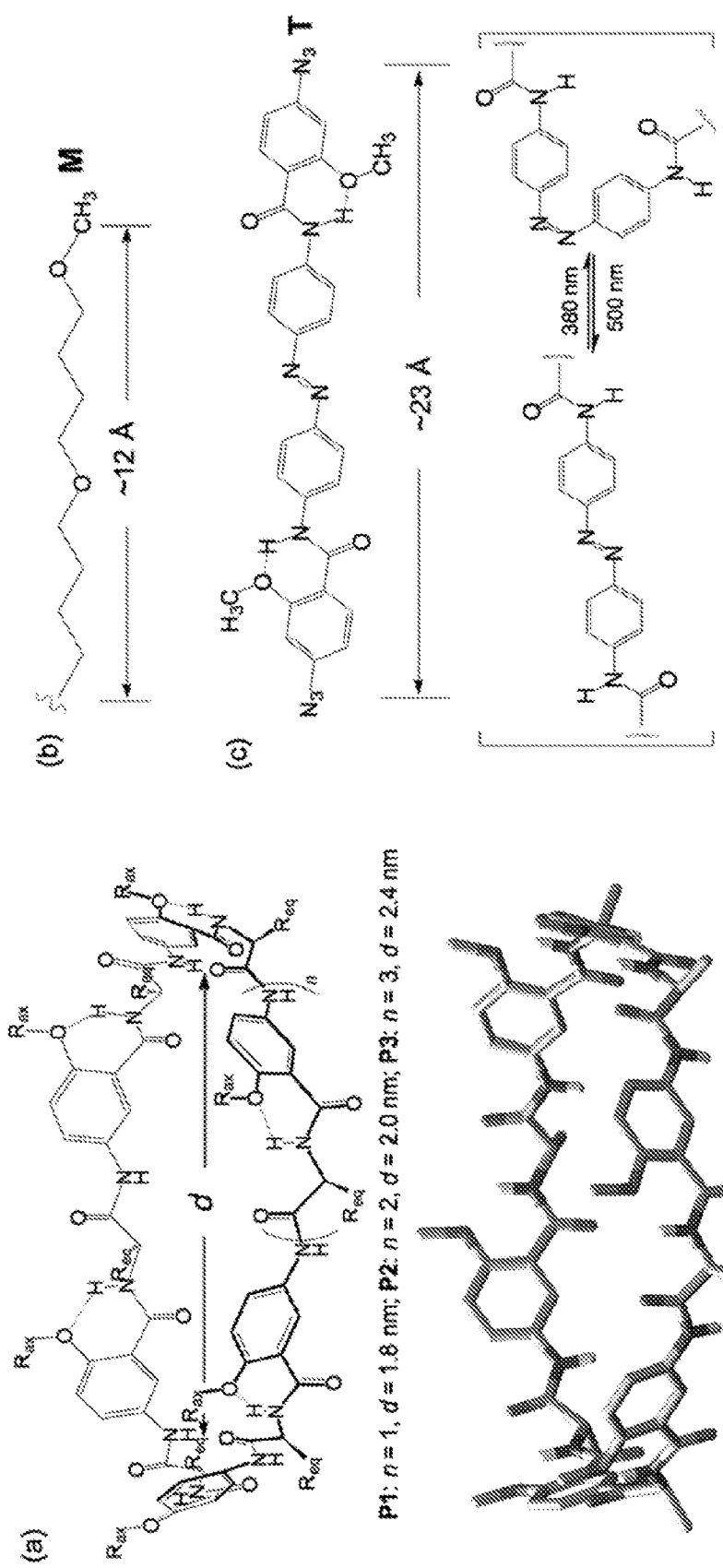
FIG. 9 shows structural design of (a) the macrocyclic portal with the energy-minimized conformation of P1 (n=1) shown, (b) the membrane-interacting tentacle and, (c) the covalent tether with the cis-trans conversion of the azobenzene unit shown. The diameter and lengths are based on the corresponding energy-minimized structures (general AMBER force field).
Figure 14:
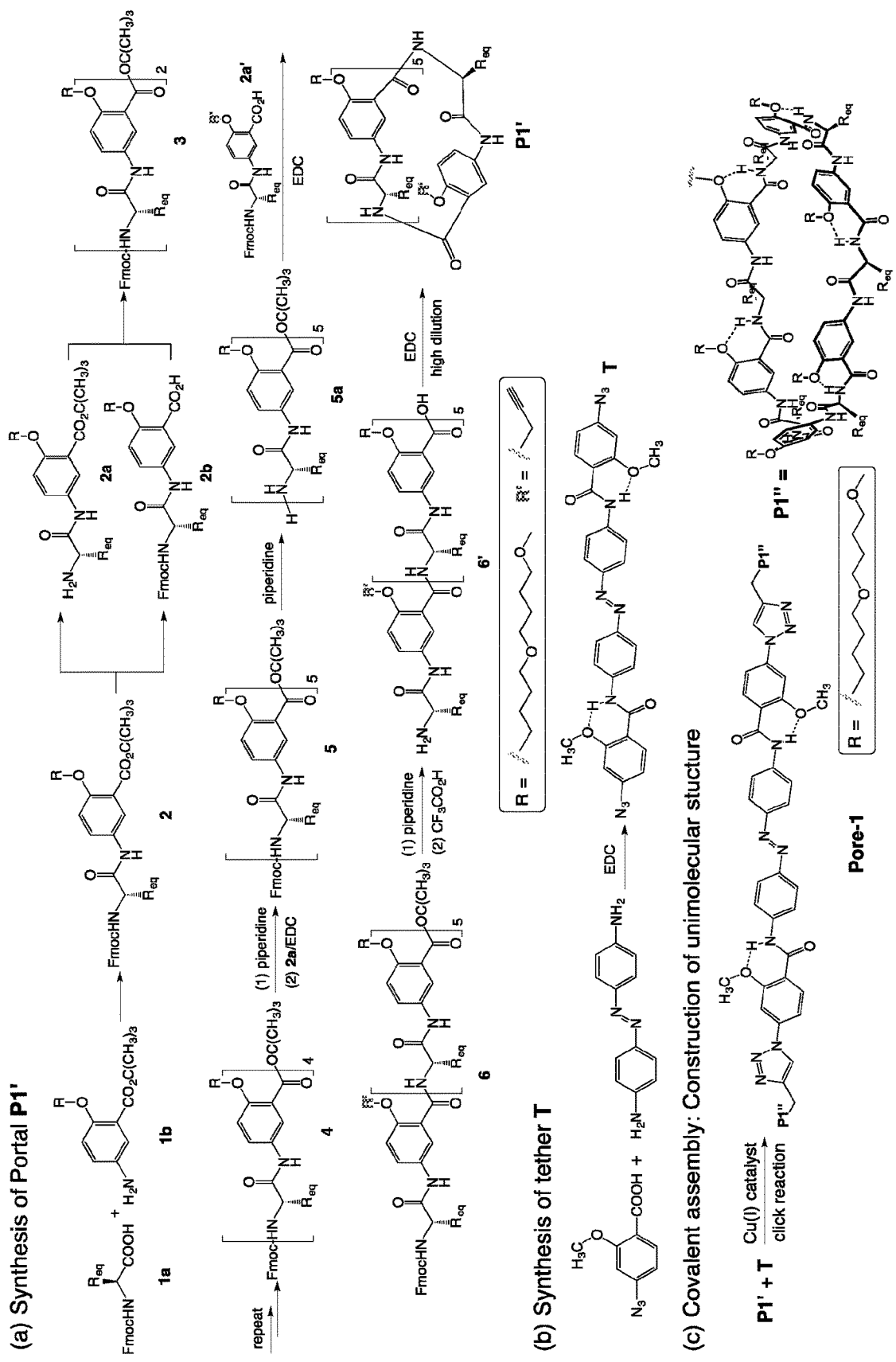
FIG. 14 provides an example of a synthesis of unimolecular pore-formers.

Design and synthesis of reversibly switchable transmembrane unimolecular pores. Structural designs. A unimolecular pore involves three modules (FIG. 9): (i) The macrocyclic portals (FIG. 9a) should have rigid or partially rigid backbones enclosing sufficiently large lumen, be connected to the covalent tether, and also offer sites for attaching the tentacles that should be parallel and point toward the same direction. Macrocycles P1-P3 are used as the cyclic portals. Based on a hybrid peptide backbone consisting of alternating α-amino acid and aromatic m-amino acid residues, the backbones of P1-P3 are overall rigid and offer defined lumen of ~1.8, 2.0, and 2.4 nm across, as revealed by the computed (energy-minimized) conformations of these macrocycles (FIG. 9a). The lumen of P1-P3 should allow the passage of a variety of molecules such as mono-, di-, and oligosaccharides. Macrocycles P1-P3 also carry axially oriented side chains ($R_{ax}$) that provide multiple sites for attaching the covalent tether and the membrane-contacting tentacles. Another set of equatorially oriented side chains ($R_{eq}$), i.e., those of the alpha-amino acid resides, offer additional structural tunability. (ii) The membrane-contacting chains or tentacles M (FIG. 9b) are based on di(butylene glycol) chains that are known to be compatible with lipid bilayers and facilitate transmembrane transport of polar species. The length (~12 Å) of M is chosen, along with each portal to which they attach, to span about half of a lipid bilayer. (iii) The membrane-spanning, photo-responsive tether T (FIG. 9c) contains a photo-switchable azobenzene moiety, which undergoes cis-trans isomerization upon applying alternative light-irradiation of about 390 nm and 500 nm. Connected to the two ends of the azobenzene unit are two benzamido units, leading to a covalent tether of ~23 Å and the final unimolecular construct of ~38 Å that matches the thickness of the lipid bilayer. Each of the benzamido moieties has a methoxy group that forms an intramolecular H-bond with the amide H, which blocks undesired intermolecular association, ensures rigidity of the tether, and helps improve solubility. The benzamido moiety of T also carries an azide group that will allow the covalent tether to be coupled to the cyclic portal via highly efficient click chemistry (FIG. 14). The overall rigidity of the covalent tether will effectively transmit the light-modulated conformational change of the azobenzene moiety to the entire unimolecular structure, and reliably switch the molecular pore between its on and off states.

Synthesis of unimolecular pore-formers. The macrocyclic portals are based on P1-P3. The uncyclized oligomeric precursors of the macrocyclic portals will be synthesized based on known method and will then be subjected to intramolecular cyclization to give macrocycles P1-P3. An example of a synthesis of unimolecular pore-former is shown in FIG. 14.

The synthesis of P1', corresponding to P1 and the final product Pore 1, are presented in FIG. 14. The synthesis of the other two portals derived from P2 and P3 follows the same steps. Coupling 1a and 1b leads to 2, which, after removing the Fmoc and t-butyl groups, gives amine 2a and acid 2b that are coupled to give 3. Subjecting 3 to the same deprotection/coupling steps results in 4, which, upon removing its Fmoc group and then couple with acid 2a, gives oligomer 5. Converting 5 into 5a followed by coupling with acid 2a' results in oligomer 6 that carries five identical di(butylene glycol) side chains R, and one side chain (R') bearing a propargyl group. Removing the Fmoc and t-butyl groups of 6 affords 6' which will be cyclized under high-dilution condition into macrocycle P1'. Tether T will be synthesized based on simple amide coupling of the corresponding 2-methoxyazidobenzoic acid with the commercially available 4, 4'-diaminoazobene. The covalent assembly of P1' (two equivalents) and tether T (one equivalent) into the final product Pore 1 will be achieved with the highly efficient, nearly quantitative "click" reaction between the alkynyl groups of P1 and the azido group of T.

Although the present disclosure has been described with respect to one or more particular embodiments and/or examples, it will be understood that other embodiments and/or examples of the present disclosure may be made without departing from the scope of the present disclosure.

---

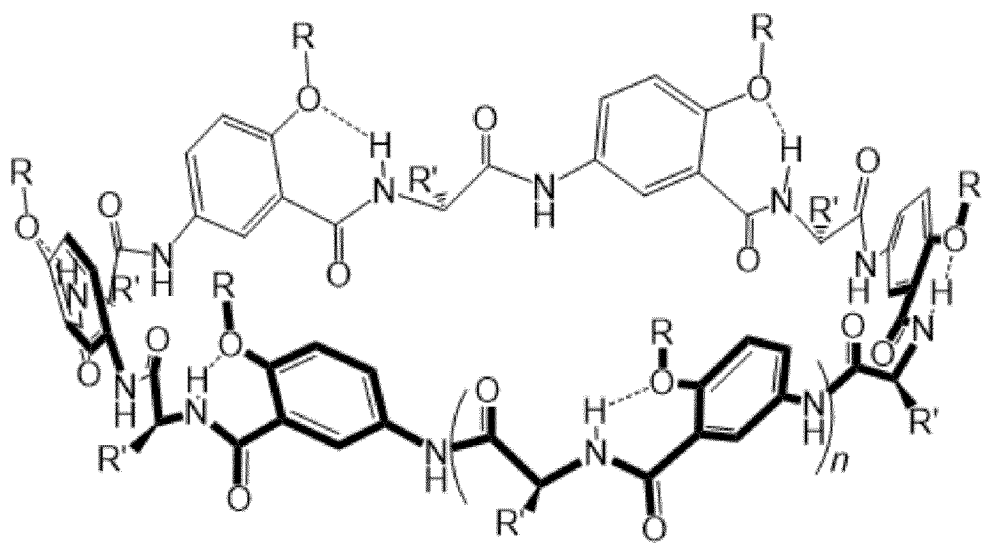

The invention claimed is:

1. A macrocyclic compound having the following structure:

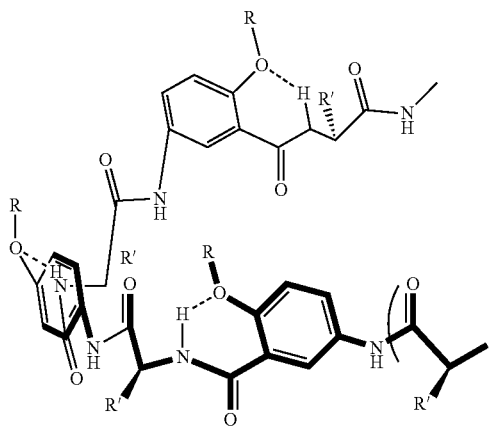

wherein R at each occurrence in the macrocyclic compound is a group comprising a transmembrane segment-thermoresponsive segment moiety;

R' is a side chain of an alpha amino acid, and optionally, one or more of the phenyl rings is substituted at the position adjacent to the ether group (—O—R) group with a group independently at each occurrence in the macrocyclic compound selected from the group consisting of aliphatic groups, halide groups, ether groups, acid groups, ester groups, and amine groups; and n is 0, 1, 2, or 3.

2. The macrocyclic compound of claim 1, wherein the transmembrane segment-thermoresponsive segment has a transmembrane segment is selected from the group consisting of alkyl moieties, transmembrane peptides and portions thereof, transmembrane proteins and portions thereof, amphiphilic alpha-helices, beta-sheets that have both a hydrophobic and a hydrophilic side, beta-sheets that have both a hydrophobic and a hydrophilic side, cylindrical amphiphilic structures, and tape-like amphiphilic structures, and combinations thereof.

3. The macrocyclic compound of claim 2, wherein the amphiphilic structures are selected from the group consisting of nystatin, amphotericin B, and alamethicin, and natural or synthetic cylindrical or tape-like amphiphilic structures.

4. The macrocyclic compound of claim 1, wherein the transmembrane segment-thermoreposive segment has a thermoresponsive segment selected from the group consisting of repeating pentapeptide with the amino acid sequence of VPGVG from the thermoresponsive elastin-like peptides (ELP), oligomers of gamma-amino acids, foldamers formed from oligomers of gamma amino acids, thermoresponsive polymers chains comprising poly(N-isopropylacrylamide) having a molecular, poly[2-(dimethylamino)ethyl methacrylate] (pDMAEMA), hydroxypropylcellulose, poly(vinylcaprolactame), or polyvinyl methyl ether.

5. The macrocyclic compound of claim 1, wherein the macrocyclic compound is in a closed configuration where the segments define a space and the macrocyclic compound further comprises a cargo disposed in the space.

6. A dimer formed from two macrocyclic units having the following structure:

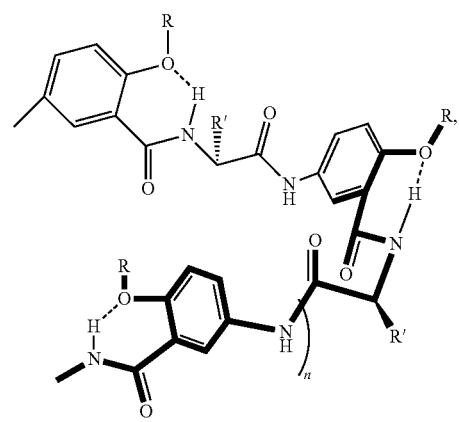

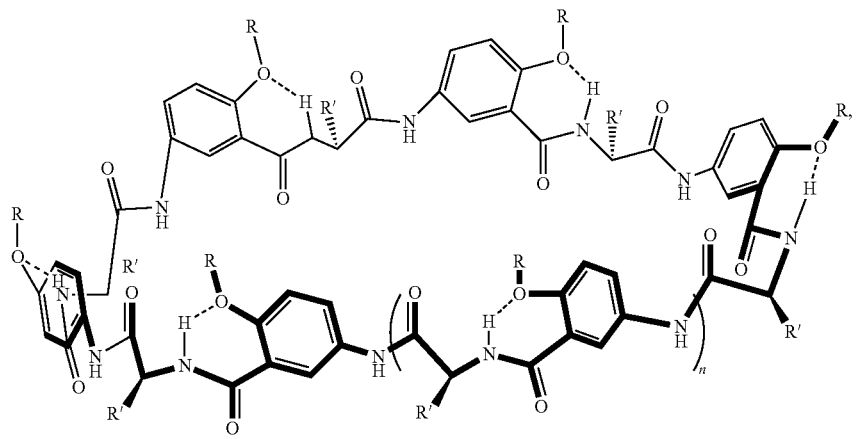

wherein R at each occurrence in the macrocyclic unit is a group comprising a transmembrane segment-thermoresponsive segment moiety or a crosslinking moiety;

R' is a side chain of an alpha amino acid, and optionally, one or more of the phenyl rings is substituted at the position adjacent to the ether group (—O—R) group with a group independently at each occurrence in the macrocyclic compound selected from the group consisting of aliphatic groups, halide groups, ether groups, acid groups, ester groups, and amine groups; and n is 0, 1, 2, or 3, wherein at least one of the R groups is a crosslinking moiety and the two macrocyclic compounds are joined by at least one crosslinking moiety.

7. The dimer of claim 6, wherein the at least one crosslinking moiety comprises a thermoresponsive moiety or a photoresponsive moiety.

8. The dimer of claim 7, wherein the photoresponsive moiety comprises an azobenzene moiety or thioindogo moiety.

9. The dimer of claim 6, wherein the transmembrane segment-thermoresponsive segment has a transmembrane segment is selected from the group consisting of alkyl moieties, transmembrane peptides and portions thereof, transmembrane proteins and portions thereof, amphiphilic alpha-helices, beta-sheets that have both a hydrophobic and a hydrophilic side, beta-sheets that have both a hydrophobic and a hydrophilic side, cylindrical amphiphilic structures, and tape-like amphiphilic structures, and combinations thereof.

10. The dimer of claim 9, wherein the amphiphilic structures are selected from the group consisting of nystatin, amphotericin B, and alamethicin, and natural or synthetic cylindrical or tape-like amphiphilic structures.

11. The dimer of claim 6, wherein the transmembrane segment-thermoresponsive segment has a thermoresponsive segment selected from the group consisting of repeating pentapeptide with the amino acid sequence of VPGVG from the thermoresponsive elastin-like peptides (ELP), oligomers of gamma-amino acids, foldamers formed from oligomers of gamma amino acids, thermoresponsive polymers chains comprising poly(N-isopropylacrylamide) having a molecular, poly[2-(dimethylamino)ethyl methacrylate] (pDMAEMA), hydroxypropylcellulose, poly(vinylcaprolactame), or polyvinyl methyl ether.

12. The dimer of claim 6, wherein one or more of the segments is covalently bonded to the macrocyclic core of one of the macrocyclic units via a linking moiety.

13. The dimer of claim 6, wherein the dimer is a bottom-to-bottom linked dimer.

14. The dimer of claim 6, wherein the dimer is a top-to-bottom linked dimer.

15. The dimer of claim 6, wherein the dimer is a top-to-top linked dimer.

* * * * *

UNITED STATES PATENT AND TRADEMARK OFFICE
CERTIFICATE OF CORRECTION

PATENT NO. : 10,781,234 B2
APPLICATION NO. : 15/763259
DATED : September 22, 2020
INVENTOR(S) : Bing Gong Page 1 of 3

It is certified that error appears in the above-identified patent and that said Letters Patent is hereby corrected as shown below:

In the Specification

Column 8, Line 28, the structure should read:

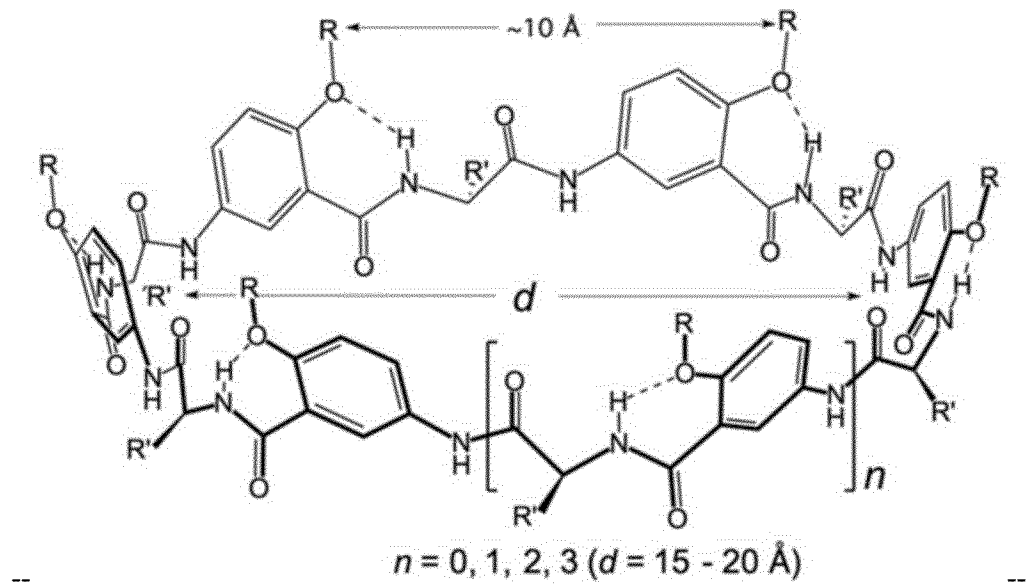

--  --

Signed and Sealed this
Thirteenth Day of April, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,781,234 B2

Column 10, last line, the structure should read:

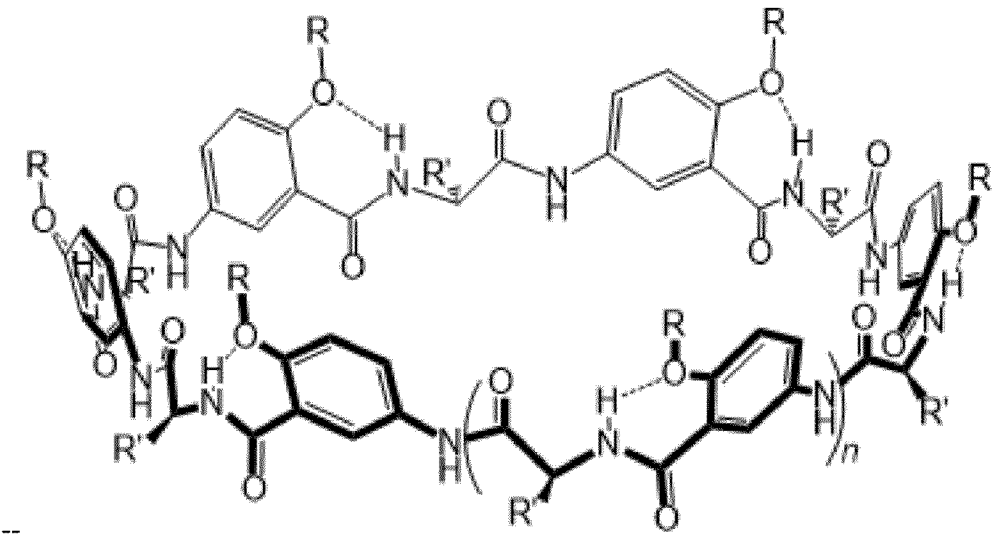

--                                                                              --

In the Claims

Column 21, Lines 25-66, in Claim 1, the structure should read:

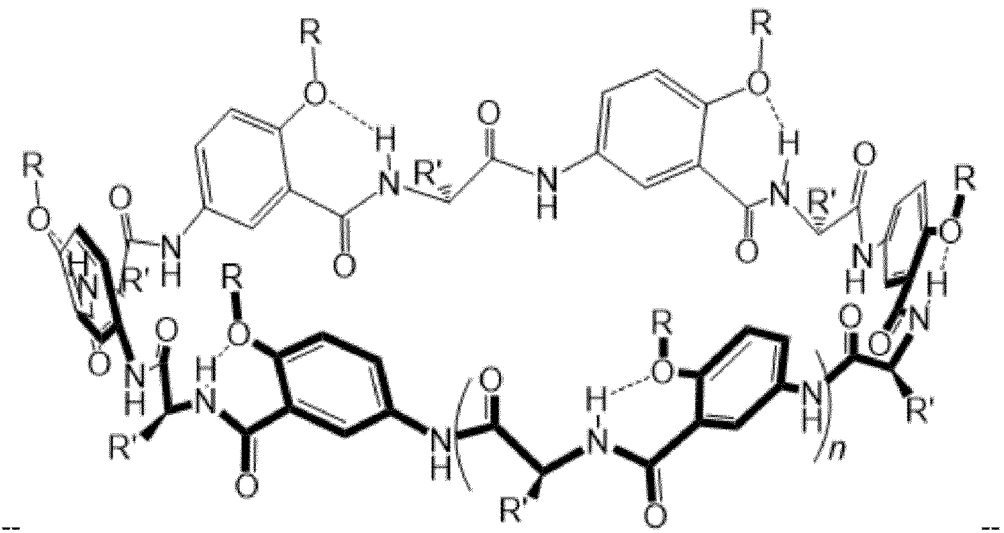

--                                                                              --

Column 23, Line 1, in Claim 6, the structure should read:

SEQUENCE LISTING

```
<160> NUMBER OF SEQ ID NOS: 5

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1

Val Pro Gly Val Pro
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide

<400> SEQUENCE: 2

Val Pro Gly Glu Gly
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide

<400> SEQUENCE: 3

Val Pro Gly Lys Gly
1               5

<210> SEQ ID NO 4
<211> LENGTH: 5
<212> TYPE: PRT
<213> ORGANISM: Artificial Sequence
<220> FEATURE:
```

```
<223> OTHER INFORMATION: Synthetic peptide

<400> SEQUENCE: 4

Ile Pro Gly Val Gly
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide

<400> SEQUENCE: 5

Val Pro Gly Val Gly
1               5
```